United States Patent [19]

Martel et al.

[11] Patent Number: 4,547,522

[45] Date of Patent: Oct. 15, 1985

[54] CYCLOPROPANE CARBOXYLIC ACID DERIVATIVES

[75] Inventors: Jacques Martel, Bondy; Jean Tessier, Vincennes; André Teche, Paris, all of France

[73] Assignee: Roussel Uclaf, Paris, France

[21] Appl. No.: 504,230

[22] Filed: Jun. 14, 1983

Related U.S. Application Data

[62] Division of Ser. No. 254,537, Apr. 15, 1981, Pat. No. 4,402,972.

[30] Foreign Application Priority Data

Apr. 16, 1980 [FR] France .............................. 80 08491
Sep. 24, 1980 [FR] France .............................. 80 20478

[51] Int. Cl.$^4$ .................... A01N 53/00; C07C 69/74
[52] U.S. Cl. ...................................... 514/531; 560/124
[58] Field of Search .................... 260/465 D; 560/124; 424/305; 514/531

[56] References Cited

U.S. PATENT DOCUMENTS 3,666,789  5/1972  Itaya et al. ....................... 424/305 X

*Primary Examiner*—Dolph H. Torrence
*Attorney, Agent, or Firm*—Bierman, Peroff & Muserlian

[57] ABSTRACT

Novel cyclopropane carboxylic acid derivatives of the formula

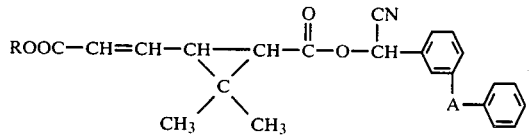

wherein A is selected from the group consisting of —O—, —CH$_2$— and

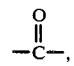

R is selected from the group consisting of alkyl of 1 to 8 carbon atoms, alkenyl and alkynyl of 2 to 8 carbon atoms and optionally unsaturated cycloalkyl and cycloalkylalkyl of 3 to 8 carbon atoms optionally substituted with at least one alkyl group and the double bond in the 3-side chain has the Z geometry in all possible stereoisomeric forms and mixtures of stereoisomers having insecticidal, nematocidal and animal and vegetable acaricidal activities and their preparation.

7 Claims, No Drawings

CYCLOPROPANE CARBOXYLIC ACID DERIVATIVES

PRIOR APPLICATION

This application is a division of our copending application Ser. No. 254,537 filed Apr. 15, 1981, now U.S. Pat. No. 4,402,972.

STATE OF THE ART

Certain derivatives of cyclopropane carboxylic acids having a lateral side chain in the 3-position of the structure

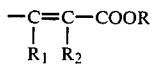   B are known but the geometry is essentially of the E form. For example, the derivatives of pyrethric acid (wherein R and $R_2$ are methyl and $R_1$ is hydrogen) are known as well as some derivatives wherein $R_1$ and $R_2$ are hydrogen. French patent No. 2,185,612 and J. Chem. Soc., Perkin I (1974), p. 2470 and Pest. Sci., Vol. 7 (1976), p. 499 describe compounds of this type. However, the side chain geometry of these compounds is predominately the E form and the process used to prepare the derivatives does not furnish exclusively the E geometry (see Agr. Biol. Chem., Vol. 34, (1970), p. 1119). For the compounds whose side chain has the geometry of the E form, they don't present any interesting properties.

OBJECTS OF THE INVENTION

It is an object of the invention to provide the novel compounds of formula I as well as a novel process for their preparation and novel intermediates.

It is another object of the invention to provide novel pesticidal compositions and to provide a novel method of combatting pests.

These and other objects and advantages of the invention will become obvious from the following detailed description.

THE INVENTION

The novel compounds of the invention are cyclopropane carboxylic acid derivatives of the formula

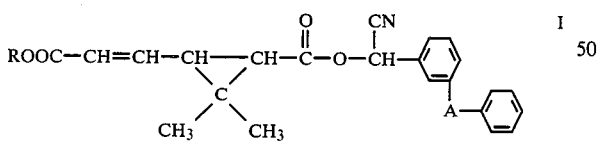   I wherein A is selected from the group consisting of —O—, —$CH_2$— and

,

R is selected from the group consisting of alkyl of 1 to 8 carbon atoms, alkenyl and alkynyl of 2 to 8 carbon atoms and optionally unsaturated cycloalkyl and cycloalkylalkyl of 3 to 8 carbon atoms optionally substituted with at least one alkyl group and the double bond in the 3-side chain has the Z geometry in all possible stereoisomeric forms and mixtures of stereoisomers.

The compounds of formula I possess 3 asymmetric carbon atoms at the 1- and 3-positions of the cyclopropane ring and the carbon atom attached to the —CN group which means the compounds of formula I have 8 stereoisomers.

In the compounds of formula I, R may be derived from a primary, secondary or tertiary alcohol and examples of R are cycloalkyl such as cyclopropyl, cyclobutyl, cyclopentyl or cyclohexyl; cycloalkylalkyl optionally substituted with at one alkyl group bonded to the COO— group such as 1-methylcyclobutyl, 1-methyl-cyclopentyl, 1-methylcyclohexyl or 2,2,3,3-tetramethylcyclopropyl; alkyl of 1 to 8 carbon atoms such as methyl, ethyl, n-propyl, isopropyl, n-butyl, isobutyl, sec-butyl, tert.-butyl, n-pentyl, tert.-pentyl, neopentyl or n-hexyl; alkenyl and alkynyl of 2 to 8 carbon atoms such as vinyl, allyl, 1,1-dimethylallyl, ethynyl or propynyl.

Among the preferred compounds of formula I are those wherein A is oxygen, those wherein the cyclopropane carboxylic acid moiety has the 1R, cis or 1R, trans structure and especially the 1R, cis structure and those wherein the alcohol moiety is derived from (S)α-cyano-3-phenoxy-benzyl alcohol. Especially preferred are those wherein R is methyl as well as those wherein R is ethyl, propyl, isopropyl or tert.-butyl.

Specific preferred compounds of formula I are (S)α-cyano-3-phenoxy-benzyl(1R,cis)2,2-dimethyl-3-[Z,2-(methoxycarbonyl)-ethenyl]-cyclopropane-carboxylate, (S)α-cyano-3-phenoxy-benzyl(1R,cis)2,2-dimethyl-3-[Z,2-(ethoxycarbonyl)-ethenyl]-cyclopropane-carboxylate, (S)α-cyano-3-phenoxy-benzyl(1R,cis)2,2-dimethyl-3-[Z,2-(isopropyloxy carbonyl)-ethenyl]-cyclopropane-carboxylate, (S)α-cyano-3-phenoxy-benzyl(1R,cis)2,2-dimethyl-3-[Z,2-(cyclopropylmethoxy carbonyl)-ethenyl]-cyclopropyl-carboxylate, (S)α-cyano-3-phenoxy-benzyl(1R,cis)2,2-dimethyl-3-[Z,2-cyclopropyloxy carbonyl)-ethenyl]-cyclopropane carboxylate and (S)α-cyano-3-phenoxy-benzyl(1R,cis)2,2-dimethyl-3-[Z,2-(tert.-butoxycarbonyl)-ethenyl]-cyclopropane carboxylate.

The novel process for the preparation of the compounds of formula I comprises reacting a compound of the formula

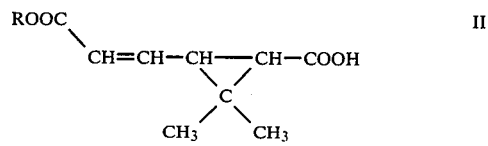   II wherein R has the above definition and the double bond has the Z geometry or a functional acid derivative thereof with an alcohol of the formula

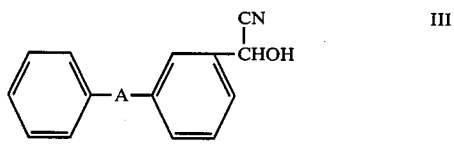   III wherein A has the above definition to obtain the corresponding compound of formula I.

In a preferred mode of the process of the invention, R in the compound of formula II is methyl and A in the alcohol is —O—. The preferred functional acid derivative is an acid halide such as the chloride.

The esterification reaction may be realized by other methods such as reacting the acid of formula II with the alcohol of formula III in the presence of dicyclohexylcarbodiimide or diisopropyl carbodiimide and the examples infra illustrate the preferred esterification processes.

The compounds of formula II are novel chemical compounds and are an object of the invention and also novel are the intermediates of formulae V, VI, VII, VIII, IX and X discussed infra used in the novel process to produce the compounds of formula II.

The said novel process of the invention to prepare the compounds of formula II comprises reacting a compound of the formula

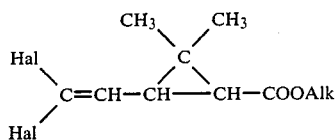    IV wherein Hal is a halogen and Alk is alkyl of 1 to 8 carbon atoms in a first step with an alkaline agent capable of pulling up the halogen atoms and in a second step (a) either with an agent capable of introducing a carboxylic group to obtain a compound of the formula

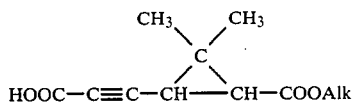    V and reacting the latter with an esterification agent to obtain a compound of the formula

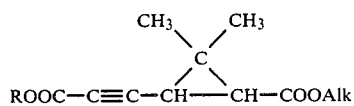    VI or (b) with an alkyl chloroformate of the formula

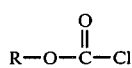    V' wherein R has the above definition to directly obtain a compound of formula VI and reacting the latter with a hydrogenation agent to obtain a compound of the formula

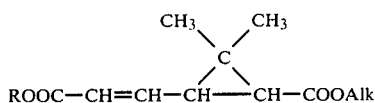    VII with the double bond having Z geometry and reacting the latter with an acid hydrolysis agent capable of selectively cleaving the 1-ester group on the cyclopropane ring to obtain the corresponding compound of formula II.

In a preferred mode of the said process, Hal is chlorine or bromine and Alk is tert.-butyl, benzyl or trityl, the alkaline agent capable of pulling up the vinylic halogens is butyllithium, the agent capable of introducing carboxylic acid group is carbon dioxide, the hydrogenation agent is hydrogen in the presence of a catalyst such as palladium in the presence of quinoline and the acid hydrolysis agent is p-toluene sulfonic acid. The said process leads with excellent yields to products having the double bond with Z geometry.

In a variation of the process to prepare the compounds of formula II, the compounds of formula V may be reduced before esterification. For example, the compound of formula V is reacted with a hydrogenation agent to obtain a compound of the formula

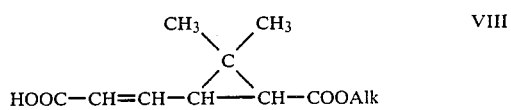    VIII with the double bond having the Z geometry and reacting the latter with an esterification agent to obtain the ester of formula VII. In a second variation of the process, the order of certain of the steps may be modified.

Another process of the invention for the preparation of the compounds of formula II, comprises reacting a compound of the formula

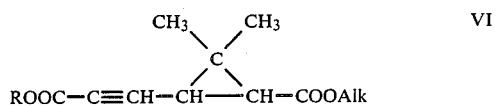    VI wherein R and Alk have the above definition is reacted with an acid hydrolysis agent capable of selectively cleaving the 1-ester group on the cyclopropane ring to obtain a compound of the formula

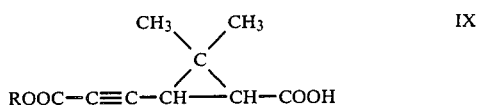    IX either reacting in the case of a functional derivative with an alcohol of formula II to obtain a compound of the formula

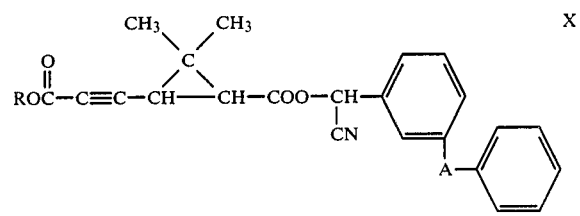    X and reacting the latter with a hydrogenation agent to obtain the corresponding compound of formula I with the double bond having the Z geometry or firsthy reacting with a hydrogenation agent to obtain the corresponding compound of formula II with the double bond having the Z geometry which in the case of a functional derivative of the acid is reacted with the alcohol of formula III to obtain the corresponding compound of formula I The preferred reaction conditions are the same as discussed above for the analogous reactions.

Another process of the invention for the preparation of the compounds of formula I comprises reacting a compound of the formula

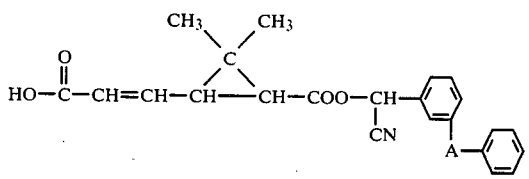

with the double bond having Z geometry with an esterification agent to obtain the corresponding compound of formula I. Preferably, the reaction is effected with a functional derivative of the alcohol such as a derivative of N,N'-diispropylurea of the formula

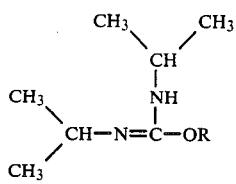

Another process of the invention for the preparation of a compound of formula XI comprises reacting the acid of formula V with 2,2,2-trichloroethanol to obtain a compound of the formula

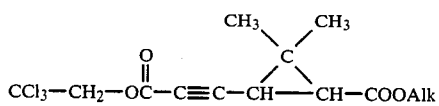

subjecting the latter compound to acid hydrolysis to obtain a compound of the formula

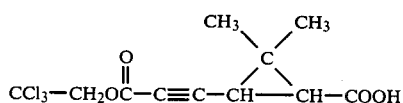

reacting the latter with an alcohol of formula III to obtain a compound of the formula

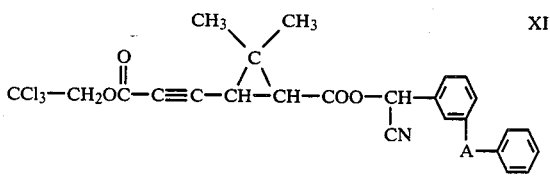

reacting the latter compound with an agent capable of cleaving the ester group containing an acetylenic carbon to obtain a compound of the formula

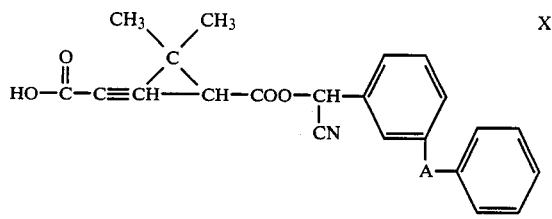

and subjecting the latter to a hydrogenation agent to obtain the corresponding compound of formula XI.

In a preferred embodiment of the said process, the Alk of the compound of formula V is tert.-butyl, benzyl or trityl, the acid hydrolysis agent is p-toluene sulfonic acid and the esterification of the compounds of formula XIII is effected with the alcohol of formula III in the presence of diisopropylcarbodiimide or dicyclohexylcarbodiimide. The clevage of the ester of formula XIV is effected with a metallic powder such as powdered zinc in an acid medium and the hydrogenation agent is hydrogen in the presence of a catalyst such as palladium in the presence of traces of quinoline. As a variation of the process, the hydrogenation and esterification steps may be reversed.

Another process of the invention for the preparation of a compound of formula I comprises reacting a compound of formula XV with an esterification agent to obtain a compound of formula X and subjecting the latter to a hydrogenation agent to obtain the corresponding compound of formula I. The preferred reaction conditions are identical to those discussed above for analogous steps.

The intermediate products produced in the process of the invention are novel intermediates and are a part of the invention and of the novel compounds of formulae XI, XII, XIII, XIV AND XV, the preferred compounds are those prepared in the specific examples infra.

The compounds of formula II are also novel products and in addition to being useful, as intermediates, they also possess interesting fungicidal properties, especially (1R,cis)2,2-dimethyl-3-[Z-2-methoxycarbonyl-ethenyl]-cyclopropane-carboxylic acid as well as bactericidal activity. They are useful for combatting fungi, especially for the control of parasitic fungi of cultivated crops such as the various parasitic fungi that attack vines, tomatoes and cucumbers. The antifungal activity of the acids has been shown in tests on Fusarium, Penicillium, Aspergilus, Geotrichum, Trichosporon and Cephalosporium.

The novel fungicidal compositions of the invention are comprised of a fungicidally effective amount of at least one acid of formula II and its salts and an inert carrier. The compositions may be in the form of powders, granules, suspensions, emulsions, solutions or other classical preparations used for fungicidal compositions and the compositions may also contain one or more other pesticidal agents.

Besides the active compounds of formula II and their salts, the compositions generally contain a vehicle and/or a nonionic, surface active agent to ensure an uniform dispersion of the ingredients of the mixture. The vehicle may be a liquid such as alcohol, water, hydrocarbons or other organic solvents or a mineral, animal or vegetable oil or a powder such as talc, clays, silicates or kieselguhr.

The antifungal compositions preferably contain 25 to 95% by weight of the active ingredient in the form of powders for spraying. 2.5 to 95% by weight of the active ingredient in the form of a powder for foliar spraying or 10 to 30% by weight of the active ingredient in the form of a liquid or solid for soil spraying.

The novel method of the invention for combatting fungi comprises contacting fungi with a fungicidally effective amount of at least one compound of formula II and its salts.

The novel bactericidal compositions of the invention are comprised of a bactericidally effective amount of at least one compound of formula II and its salts and an inert carrier. The compositions may be in the form of powders, suspensions, emulsions or solutions and may contain other pesticidal agents. Besides the active ingredient, the compositions may contain a liquid or solid vehicle and/or a surface active agent as discussed above. The bactericidal activity has been shown on glues infested with a complex mixture of bacteria. The compositions usually contain 20 to 95% by weight of the active ingredient.

The bactericidal compositions of the invention are generally useful as industrial biocides, especially for the protection of glues, of industrial charges and are utilized in cutting oils. They are equally useful to prevent and eliminate the formation of microbial slime in paper circuits or for the treatment of skins, tanning liquors and hides.

The novel method of the invention for combatting bacteria comprises contacting bacteria with a bactericidally effective amount of at least one compound of formula II and its salts.

The pesticidal compositions of the invention are comprised of a pesticidally effective amount of at least one compound of formula I and an inert carrier. The compositions are useful for combatting vegetable parasites, domestic parasites and parasites of warm-blooded animals. They are useful for combatting insects, nematodes, vegetable acariens and animal acariens.

The compositions of the invention are especially useful as insecticides against insects in the agricultural field and are useful against aphides lepidoptera and coleoptera larvae, for instance. They are usually used at a dose of 10 to 300 g of active ingredients per hectare. In addition, the compositions have a good insect lethal activity and an excellent knock-down power and are photostable and non-toxic to mammals.

These properties of the compositions of the invention correspond perfectly to the needs of the modern agrochemical industry and make them useful to protect crops without harming the environment. (S)α-cyano-3-phenoxy-benzyl(1R,cis)2,2-dimethyl-3-[Z-2-methoxycarbonyl-ethenyl]-cyclopropane-1-carboxylate has a particularly remarkable insecticidal activity. The insecticidal compositions are also useful to combat domestic insects such as flies, mosquitoes and beetles.

The pesticidal compositions of the invention are also useful for combatting vegetable acariens and parasitic nematodes such as Tetranychus Urticae.

The pesticidal compositions of the invention are also useful for combatting animal parasites such as ticks and especially ticks of the Boophilus species, of the Hyalomnia species, of the Amblyomnia species and of the Rhipicephalus species and for combatting all sorts of scabies, especially sarcoptic scabies, psoroptic and chorioptic scabies.

Among the preferred pesticidal compositions of the invention arethose wherein the active principle is one of the group consisting of (S)α-cyano-3-phenoxy-benzyl(1R,cis)2,2-dimethyl-3-[Z-2-(methoxycarbonyl)-ethenyl]-cyclopropanecarboxylate, (S)α-cyano-3-phenoxy-benzyl(1R,cis)2,2-dimethyl-3-[Z-2(ethoxycarbonyl)-ethenyl]-cyclopropane-carboxylate, (S)α-cyano-3-phenoxy-benzyl(1R,cis)2,2-dimethyl-3-[Z-2-(isopropyloxycarbonyl)-ethenyl]-cyclopropane-carboxylate, (S)α-cyano-3-phenoxy-benzyl(1R,cis)2,2-dimethyl-3-[Z-2-(cyclopropylmethoxycarbonyl)-ethenyl]-cyclopropane-carboxylate, (S)α-cyano-3-phenoxy-benzyl(1R,cis)2,2-dimethyl-3-[Z-2-(cyclopropyloxycarbonyl)-ethenyl]-cyclopropane-carboxylate and (S)α-cyano-3-phenoxy-benzyl(1R,cis)2,2-dimethyl-3-[Z-2-(tert.-butoxycarbonyl)-ethenyl]-cyclopropane-carboxylate.

The compositions destined for agrochemical and domestic usage may contain more than one active agent and may also contain other pesticides. The said compositions may be in the form of powders, granules, suspensions, emulsions, solutions, aerosol solutions, combustible strips, or other classical preparatives used for compositions of this nature.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for domestic use, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably, In the case of a serpentine insecticide, the inert support may be made, for example, of pyrethrum stalks, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for household use may be prepared as a spraying oil containing the active ingredient and the oil may soak the wick of a lamp which is then subjected to combustion. The concentration of the compound of formula I in the oil is preferably 0.03 to 95% by weight.

The acaricidal and nematocidal compositions of the invention may also contain one or more other pesticides and are in the usual powder, granules, suspension, emulsion or solution form. For acaricide use, the compositions are preferably wettable powders for foliar spraying containing 1 to 80g% of liquids for foliar spraying containing 1 to 500 g/l of the active ingredient. Also useful are powders for foliar powdering containing 0.5 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene(piperonyl butoxide) or N-(2-ethyl-heptyl)bicyclo-[2,2-1]-5-heptene-2,3-dicarboximide or piperonyl-bis-2-(2-n-butoxy-ethoxy)-ethyl acetal (tropital).

When the compositions are to be used to combat animal parasitic acariens, the active compounds of formula I are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, of meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevert or treat scabies. The compositions may also be used as anthelmintics.

The said medicaments may be administered externally by vaporization, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal compositions containing as an active ingredient at least one compound of formula I and as a second active ingredient at least one pyrethrinoid ester selected from the group consisting of esters of allethrolone, of 3,4,5,6-tetrahydrophthaliminomethyl alcohol, of 5-benzyl-3-furylmethyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols and 2,2-dimethyl-3-(2,2-dichlorovinyl)cyclopropane-1-carboxylic acids, esters of α-cyano-3-phenoxybenzyl alcohols and 2,2-dimethyl-3-(2,2-dibromovinyl)-cyclopropane-1-carboxylic acids, esters of 3-phenoxy-benzyl alcohol and 2-p-chlorophenyl-2-isopropyl-acetic acids, esters of allethrolones, 3,4,5,6-tetrahydrophthalimidomethyl alcohol, 5-benzyl-3-furyl-methyl alcohol, 3-phenoxy-benzyl alcohol or α-cyano-3-phenoxy-benzyl alcohols and 2,2-dimethyl-3-(1,2,2,2-tetrahaloethyl)-cyclopropane-1-carboxylic acids where halo is fluorine, chlorine or bromine wherein the compounds of formula I are in all possible stereoisomer forms of the acids and alcohols of the pyrethrinoid esters.

The latter associated compositions of the invention are of particular interest for combatting by the polyvalence of their action a larger range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it is to be understood that the invention is not intended to be limited to the specific embodiments.

EXAMPLE 1

(S)α-cyano-3-phenoxy-benzyl(1R,cis)2,2-dimethyl-3-[Z-2-methoxy carbonyl-ethenyl]-cyclopropane-carboxylate STEP A:
Tert.-butyl(1R,cis)2,2-dimethyl-3-[2-(methoxycarbonyl)-ethynyl]-cyclopropane-carboxylate 55 g of tert-butyl(1R,cis)2,2-dimethyl-3-(2,2-dibromovinyl)-cyclopropane-carboxylate were introduced into 550 cm$^3$ of tetrahydrofuran and the mixture was cooled to −70° C. 132 cm$^3$ of a 20% solution of butyllithium in cyclohexane were added over 40 minutes to the mixture which was stirred for 30 minutes at −65° C. 12.5 cm$^3$ of methyl chloroformate were then added thereto and after 2 hours reaction at −70° C., the temperature was allowed to rise again to −20° C. The mixture was poured into an aqueous solution of monosodium phosphate and the mixture was extracted with ether. The organic phase was washed, dried and evaporated to dryness under reduced pressure. 38.3 g of the residue were chromatographed over silica gel and was eluted with an 8–2 cyclohexane-ethyl acetate mixture to obtain 17.2 g of tert.-butyl(1R,cis)2,2-dimethyl-3-[2-(methoxy carbonyl)-ethynyl]-cyclopropane-carboxylate.

STEP B:
Tert.-butyl(1R,cis)2,2-dimethyl-3-[(Z)-2-(methoxy carbonyl)-ethenyl]-cyclopropane-carboxylate 12 g of the product of Step A in 240 cm$^3$ of ethyl acetate were hydrogenated in the presence of 2.4 g of 10% palladium hydroxide on barium sulfate and 2.4 cm$^3$ of quinoline. The mixture was filtered and the filtrate was evaporated to dryness to obtain 11 g of tert.-butyl(1R,cis)2,2-dimethyl-3-[(Z)-2-(methoxy carbonyl)-ethenyl]-cyclopropane carboxylate.

STEP C: (1R,cis)2,2-dimethyl-3-[(Z)-2-(methoxy carbonyl)-ethenyl]-cyclopropane-carboxylic acid A solution containing 13.5 g of the product of Step B, 100 cm$^3$ of toluene and 400 mg of hydrated p-toluene sulfonic acid was refluxed for 3 hours and then was evaporated to dryness under reduced pressure. The 11.2 g of residue were chromatographed over silica gel and was eluted with a 60–39–1 cyclohexane-ethyl acetate-acetic acid mixture. The eluate was evaporated to dryness under reduced pressure to obtain 9.6 g of (1R, cis)2,2-dimethyl-3-[(Z)-2-(methoxy carbonyl)-ethenyl]-cyclopropane-carboxylic acid melting at 110° C. and having a specific rotation of $[\alpha]_D^{20} = +75.5° \pm 2°$ (c=1% in CHCl$_3$).

NMR Spectrum CDCl$_3$: Peaks at 1.3 ppm (protons of 2-methyls of cyclopropane); at 1.86–2 ppm (proton of cyclopropane); at 3.1–3.28–3.43 ppm (proton of cyclopropane); at 5.8–5.99 ppm (ethylenic proton α to CO$_2$CH$_3$); at 6.42–6.58 ppm and 6.61–6.77 ppm (ethylenic proton β to CO$_2$CH$_3$); at 8.63 ppm (proton of CO$_2$H); at 3.71 ppm (protons of methoxy).

STEP D:
(S)α-cyano-3-phenoxy-benzyl(1R,cis)2,2-dimethyl-3-[Z-2-(methoxycarbonyl)-ethenyl]-cyclopropane-carboxylate 7 g of the product of Step C, 7.3 g of dicyclohexylcarbodiiumide and 3 ml of pyridine were added to 50 ml of methylene chloride and after the addition of 8 g of (S)α-cyano-3-phenoxy-benzyl alcohol, the mixture was stirred at room temperature for 16 hours. The mixture was filtered and the filtrate was evaporated to dryness under reduced pressure. The 20 g of residue were crystallized from isopropyl ether to obtain 10.5 g of (S)α-cyano-3-phenoxy-benzyl(1R,cis)2,2-dimethyl-3-[Z-2-(methoxycarbonyl)-ethenyl]-cyclopropane-carboxylate melting at 98° C.

NMR Spectrum (deuterochloroform): Peaks at 1.23 and 1.26 ppm (hydrogens of 2-methyls); at 1.93–2.07 ppm (1-hydrogen); at 3.2–3.34–3.37–3.50 ppm (3-hydrogen); at 6.35 ppm (hydrogen on carbon attached to —CN); at 5.8 to 6.05 ppm

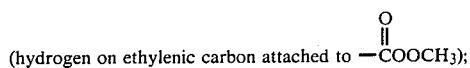
(hydrogen on ethylenic carbon attached to —COOCH₃);

at 6.35–6.51 ppm and 6.55–6.72 ppm (hydrogen of ethylenic carbon α to the cyclopropane ring); at 3.72 ppm

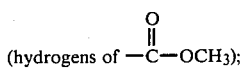
(hydrogens of —C—OCH₃);

at 6.9 to 7.6 ppm (aromatic hydrogens).

EXAMPLE 2

(R)α-cyano-3-phenoxy-benzyl(1R,cis)2,2-dimethyl-3-[Z-2-(methoxycarbonyl)-ethenyl]-cyclopropane carboxylate Using the procedure of Step D of Example 1, 1.5 g of (1R, cis)2,2-dimethyl-3-([Z-2-(methoxycarbonyl)-ethenyl]cyclopropane carboxylic acid and 1.9 g of (R)α-cyano-3-phenoxybenzyl alcohol were reacted to obtain 4.3 g of raw product. The latter was chromatographed over silica gel and was eluted with a 9-1 cyclohexane-ethyl acetate mixture to obtain 2.5 g of (R)α-cyano-3-phenoxy-benzyl(1R,cis)2,2-dimethyl-3-[Z-2-(methoxycarbonyl)-ethenyl]-cyclopropane carboxylate with a specific rotation of $[\alpha]_D^{20} = +23.5° \pm 2.5°$ (c=0.5% in benzene).

NMR Spectrum (deuterochloroform): Peaks at 1.32 ppm (hydrogens of geminal methyls); at 1.92–2.06 ppm (1-hydrogen); at 3.17 to 3.45 ppm (3-hydrogen); at 6.3 ppm (hydrogen on carbon attached to —CN); at 5.8–5.98 ppm (hydrogen of ethylenic carbon attached to —COOCH₃); at 6.3 to 6.7 ppm (hydrogen of ethylenic carbon α to cyclopropane ring); at 3.7 ppm

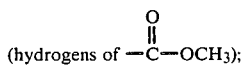
(hydrogens of —C—OCH₃);

at 6.9 to 7.6 ppm (aromatic hydrogens).

EXAMPLE 3

(S)α-cyano-3-phenoxy-benzyl(1R,cis)2,2-dimethyl-3-[Z-2-(ethoxycarbonyl)-ethenyl]-cyclopropane-carboxylate STEP A: Tert.-butyl(1R,cis)2,2-dimethyl-3-(carboxy ethynyl)cyclopropane-carboxylate 60 ml of 20% solution of butyllithium in cyclohexane were added at −65° C. to a mixture of 26 g of tert.-butyl(1R,cis)2,2-dimethyl-2-(2,2-dibromovinyl)-cyclopropane-carboxylate and 175 ml of anhydrous tetrahydrofuran and the mixture was stirred at −60° C. for one hour after which carbon dioxide was bubbled therethrough for 90 minutes. The mixture was poured into iced N sodium hydroxide solution and the pH of the aqueous phase was adjusted to 4. The mixture was extracted with ether and the organic phase was dried and evaporated to dryness under reduced pressure. The residue was crystallized from petroleum ether (b.p.=60°–80° C.) to obtain 8.3 g of tert.-butyl(1R,cis)2,2-dimethyl-3-(carboxylethynyl)-cyclopropane-carboxylate melting at 144° C.

NMR Spectrum (deuterochloroform): Peaks at 1.22 and 1.37 ppm (hydrogens of geminal methyls); at 1.78 ppm (1- and 3-hydrogens of cyclopropane); at 1.47 ppm (hydrogens of tert.-butyl); at 8.25 ppm (hydrogen of —COOH).

STEP B:

Tert.-butyl(1R,cis)2,2-dimethyl-3-(ethoxycarbonyl ethynyl)-cyclopropane-carboxylate 4 g of the product of Step A, 3.4 g of dicyclohexyl-carbodiiumide and 6 mg of 4-dimethylamino-pyridine were added to 30 ml of methylene chloride followed by the addition of 1.5 ml of ethanol and the mixture was stirred at 20° C. for 16 hours. The mixture was filtered and the filtrate was evaporated to dryness under reduced pressure. The residue was chromatographed over silica gel and was eluted with a 9-1 cyclohexane-ethyl acetate mixture to obtain 4.25 g of tert.butyl (1R, cis)2,2-dimethyl-3-(ethoxycarbonyl-ethynyl)-cyclopropane-carboxylate.

NMR Spectrum (deuterochloroform): Peaks at 1.18–1.21 ppm and 1.36–1.47 ppm (hydrogens of geminal methyls); at 1.73 and 1.82 ppm (1- and 3-hydrogens of cyclopropane ring); at 1.47 ppm (hydrogens of tert.-butyl); at 1.27–1.38–1.5 ppm and 4.0–4.13–4.25–4.36 ppm (hydrogens of ethyl).

STEP C:

Tert.-butyl(1R,cis)2,2-dimethyl-3-[Z-2-(ethoxycarbonyl)-ethenyl]-cyclopropane-carboxylate A mixture of 4.3 g of the product of Step B, 100 ml of ethyl acetate, 800 mg of palladium hydroxide on barium sulfate and 0.8 ml of quinoline was hydrogenated and the mixture was then filtered. The filtrate was made acidic by addition of 2N hydrochloric acid and was washed with water. The organic phase was dried and evaporated to dryness to obtain 4.6 g of residue. The latter was chromatographed over silica gel and was eluted with a 95-5 cyclohexane-ethyl acetate mixture to obtain 2.5 g of tert.-butyl(1R, cis)2,2-dimethyl-3-[Z-2-(ethoxy-carbonyl)-ethenyl]-cyclopropane-carboxylate.

NMR Spectrum (deuterochloroform): Peaks at 1.25 and 1.28 ppm (hydrogens of geminal methyls); at 1.78–1.93 ppm (1-hydrogen of cyclopropane); at 2.98–3.1–3.2 ppm (3-hydrogen of cyclopropane); at 6.4–6.6–6.8 ppm (hydrogen of ethylenic carbon α to cyclopropane); at 5.7–5.9 ppm (hydrogen of ethylenic carbon attached to —COOCH₂—CH₃); at 4.4–4.13–4.25–4.36 ppm (hydrogen of —CH₂— of —O—CH₂—CH₃).

STEP D:

(1R,cis)2,2-dimethyl-3-[Z-2-(ethoxycarbonyl)ethenyl]-cyclopropane-carboxylic acid A mixture of 2.3 g of the product of Step C, 20 mg of hydrated p-toluene sulfonic acid and 20 ml of toluene was refluxed for 40 minutes and the mixture was then evaporated to dryness under reduced pressure. The 2.1 g of residue were chromatographed over silica gel and were eluted with a 60-39-1 cyclohexane-ethyl acetate-acetic acid mixture to obtain 1.5 g of (1R,cis)2,2-dimethyl-3-[Z-2-(ethoxycarbonyl)-ethenyl]-cyclopropane-carboxylic acid melting at 96° C.

NMR Spectrum (deutereochloroform): Peaks at 1.3 and 1.32 ppm (hydrogens of geminal methyls); at 1.86–2.02 ppm (1-hydrogen of cyclopropane); at 3.15–3.28 ppm and 3.3–3.45 ppm (3-hydrogen of cyclopropane); at 6.38–6.53 ppm and 6.55–6.73 ppm (hydrogen of ethylenic carbon on cyclopropane); at 5.78–5.96 ppm (hydrogen of ethylenic carbon attached to —COOCH$_2$—CH$_3$); at 1.18-1.3-1.41 ppm (hydrogens of methyl of —COOCH$_2$—CH$_3$); at 4.0-4.13 ppm and 4.25-4.36 ppm (hydrogens of methylene of —COOCH$_2$—CH$_3$).

STEP E:

(S)α-cyano-3-phenoxy-benzyl(1R,cis)2,2-dimethyl-3-[Z-2-(ethoxycarbonyl)-ethenyl]-cyclopropane-carboxylate Using the procedure of Step D of Example 1, 1.25 g of the product of Step D and 1.45 g of (S)α-cyano-3-phenoxybenzyl alcohol were reacted to obtain 4.1 g of raw product which was chromatographed over silica gel. Elution with a 9-1 cyclohexane-ethyl acetate mixture yielded 1.95 g of (S)α-cyano-3-phenoxy-benzyl(1R,cis)2,2-dimethyl-3-[Z-2-(ethoxycarbonyl)-ethenyl]-cyclopropane-carboxylate with a specific rotation of $[\alpha]_D^{20} = +57.5° \pm 3°$ (c=0.3% in benzene).

NMR Spectrum (deuterochloroform): Peaks at 1.25-1.27 ppm (hydrogens of geminal methyls); at 1.92-2.06 ppm (1-hydrogen of cyclopropane); at 3.2-3.36 ppm and 3.8-3.52 ppm (3-hydrogen of cyclopropane); at 5.83-6.03 ppm (hydrogen on ethylenic carbon attached to —COOCH$_2$—CH$_3$); at 6.38-6.73 ppm (hydrogen of ethylenic carbon α to cyclopropane); at 6.35 ppm (hydrogen on carbon attached to —CN); at 1.18-1.3-1.41 ppm (hydrogen of methyl of —CH$_2$—CH$_3$); at 4.01-4.13-4.25-4.36 ppm (hydrogen of —CH$_2$— of —CH$_2$—CH$_3$).

EXAMPLE 4

(S)α-cyano-3-phenoxy-benzyl(1R,cis)2,2-dimethyl-3-[Z-2-(n-propoxycarbonyl)-ethenyl]-cyclopropane-carboxylate

STEP A:

Tert.-butyl(1R,cis)2,2-dimethyl-3-[n-propoxycarbonylethynyl]-cyclopropane-carboxylate 55 ml of 20% solution of butyllithium in cyclohexane were added at −60° C. to a mixture of 22.8 g of tert.-butyl(1R,cis)2,2-dimethyl-3-[Z-2-dibromovinyl]-cyclopropane-carboxylate and 250 ml of tetrahydrofuran and the mixture was held at −65° C. for one hour after which 8 ml of n-propyl chloroformate were added thereto at −65° C. over 15 minutes. The mixture was stirred at −65° C. for one hour and the temperature was allowed to rise over one hour to room temperature. The mixture was stirred at room temperature for one hour and was then poured with stirring into a saturated aqueous monosodium phosphate solution. The mixture was extracted with ether and the organic phase was washed with water, dried, evaporated to to dryness under reduced pressure. The 19.5 gm of oil residue were chromatographed over silica gel and eluted with a 9-1 cyclohexane-ethyl acetate mixture to obtain 11.5 g of tert.-butyl(1R,cis)2,2-dimethyl-3-[n-propoxycarbonylethynyl]-cyclopropane-carboxylate.

NMR Spectrum (deuterochloroform): Peaks at 1.17 and 1.37 ppm (hydrogens of geminal methyls); at 1.72 ppm (1- and 3-hydrogens of cyclopropane); at 1.44 ppm (hydrogens of tert.-butyl); at 4.0-4.12-4.23 ppm (hydrogen of 1—CH$_2$— of —COOCH$_2$—CH$_3$); at 0.83-0.95-1.06 ppm (hydrogens of methyl of —COOCH$_2$—CH$_2$—CH$_3$).

STEP B:

Tert.-butyl(1R,cis)2,2-dimethyl-3-[Z-2-(n-propoxycarbonyl)-ethenyl]-cyclopropane-carboxylate A mixture of 7 g of the product of Step A, 140 ml of ethyl acetate, 1.4 g of 10% palladium hydroxide on barium sulfate and 1.4 ml of quinoline was hydrogenated and was then filtered. The filtrate was washed with 2N hydrochloric acid and with water, dried and evaporated to dryness under reduced pressure. The 7.2 g of residue were chromatographed over silica gel and eluted with a 95-5 cyclohexane-ethyl acetate mixture to obtain 6.1 g of tert.-butyl(1R,cis)2,2-dimethyl-3-[Z-2-(n-propoxycarbonyl)-ethenyl]-cyclopropane-carboxylate.

NMR Spectrum (deuterochloroform): Peaks at 1.25 and 1.29 ppm (hydrogens of geminal methyls); at 1.5 to 2.03 ppm (1-hydrogen of cyclopropane); at 3.03 to 3.35 ppm (3-hydrogen of cyclopropane); at 6.5-6.66 ppm and 6.69-6.85 ppm (hydrogen of ethylenic carbon attached to cyclopropane); at 5.82-6.0 ppm (hydrogen of carbon attached to —COOCH$_2$—CH$_2$—CH$_3$); at 4.02-4.12-4.23 ppm (hydrogen of 1—CH$_2$— of COOCH$_2$—CH$_2$—CH$_3$); at 0.86-0.98-1.1 ppm (hydrogen of —CH$_3$ of —COOCH$_2$—CH$_2$—CH$_3$).

STEP C:

(1R,cis)2,2-dimethyl-3-[Z-2-(n-propoxycarbonyl)ethenyl]-cyclopropane-carboxylic acid A mixture of 5.8 g of the product of Step B, 200 mg of hydrated p-toluene sulfonic acid and 60 ml of toluene was refluxed for one hour and was then evaporated to dryness under reduced pressure. The 5 g of residue were chromatographed over silica gel and eluted with a 70-29-1 cyclohexane-ethyl acetate-acetic acid mixture to obtain 4.2 g of (1R,cis)2,2-dimethyl-3-[Z-2-(n-propoxycarbonyl)-ethenyl]-cyclopropanecarboxylic acid.

NMR Spectrum (deuterochloroform): Peaks at 1.27 and 1.29 ppm (hydrogens of geminal methyls); at 1.86-2 ppm (1-hydrogen of cyclopropane); at 3.13 to 3.45 ppm (3-hydrogen of cyclopropane); at 5.8-6 ppm (hydrogen of ethylenic carbon attached to —COOCH$_2$—CH$_2$—CH$_3$); at 6.4-6.56-6.59 ppm (hydrogen of ethylenic carbon attached to cyclopropane); at 3.98-4.08-4.18 ppm (hydrogen of 1—CH$_2$— of —COOCH$_2$—CH$_2$—CH$_3$); at 0.83-0.95-1.06 ppm (hydrogen of —CH$_3$ of —COOCH$_2$—CH$_2$—CH$_3$).

STEP D:

(S)α-cyano-3-phenoxy-benzyl(1R,cis)2,2-dimethyl-3-[Z-2-(n-propoxycarbonyl)-ethenyl]-cyclopropane-carboxylate Using the procedure of Step D of Example 1, 1.5 g of the product of Step C and 1.7 g of (S)α-cyano-3-phenoxybenzyl alcohol were reacted to obtain 4.1 g of raw product which was chromatographed over silica gel. Elution with a 7-3 n-hexane-isopropyl ether mixture yielded 2.2 g of (S)α-cyano-3-phenoxy-benzyl(1R,cis)2,2-dimethyl-3-[Z-2-(n-propoxycarbonyl)-ethenyl]-cyclopropane-carboxylate with a specific rotation of $[\alpha]_D^{20} = +52° \pm 2.5°$ (c=0.5% in benzene).

NMR Spectrum (deuterochloroform): Peaks at 1.25-1.28 ppm (hydrogens of geminal methyls); at 1.94-2.03 ppm (1-hydrogen of cyclopropane); at 3.29-3.39-3.49 ppm (3-hydrogen of cyclopropane); at 6.33 ppm (hydrogen on carbon attached to —CN); at 5.89-6.01 ppm (hydrogen on ethylenic carbon attached to —COOCH$_2$—CH$_2$—CH$_3$); at 6.41-6.52 ppm and 6.53–6.64 ppm (hydrogen of branched ethylenic carbon on cyclopropane); at 4.02–4.09–4.15 ppm (hydrogen of 1—CH$_2$— of —COOCH$_2$—CH$_2$—CH$_3$); at 0.88–0.96–1.04 ppm (hydrogen of —CH$_3$ of —COOCH$_2$—CH$_2$—CH$_3$).

EXAMPLE 5

(S)α-cyano-3-phenoxy-benzyl(1R,cis)2,2-dimethyl-3-[Z-2-(isopropoxycarbonyl)-ethenyl]-cyclopropane-carboxylate

STEP A:
Tert.-butyl(1R,cis)2,2-dimethyl-3-[Z-2-carboxyethenyl]-cyclopropane-carboxylate A mixture of 2 g of tert.-butyl(1R,cis)2,2-dimethyl-3-[Z-carboxyethynyl]-cyclopropane-carboxylic acid, 40 ml of ethyl acetate, 0.38 g of 10% palladium hydroxide on barium sulfate and 0.4 ml of quinoline was hydrogenated and was filtered. The filtrate was washed with 0.5N hydrochloric acid and with water until the wash water was neutral, dried and evaporated to dryness under reduced pressure to obtain 2 g of tert.-butyl(1R,cis)2,2-dimethyl-3-[Z-2-carboxyethenyl]-cyclopropane-carboxylate melting at 94° C.

STEP B:
Tert.-butyl(1R,cis)2,2-dimethyl-3-[Z-2-(isopropoxycarbonyl)-ethenyl]-cyclopropane-carboxylate 2 g of O-isopropyl-N,N'-diisopropyl-isourea were added to a mixture of 2.7 g of the product of Step A and 10 ml of ethyl acetate and the mixture was stirred at room temperature for one hour, refluxed for 90 minutes and then cooled to 20° C. The mixture was filtered and the filtrate was evaporated to dryness under reduced pressure. The 3.5 g of oil residue were chromatographed over silica gel and eluted with a 7–3 benzene-cyclohexane mixture to obtain 1 g of tert.-butyl(1R,cis)2,2-dimethyl-3-[Z-2-(isopropoxycarbonyl)-ethenyl]-cyclopropane-carboxylate which was used as is for the next step.

STEP C:
(1R,cis)2,2-dimethyl-3-[Z-2-(isopropoxycarbonyl)ethenyl]-cyclopropane-carboxylic acid A mixture of 1.4 g of the product of Step B, 100 mg of p-toluene sulfonic acid and 14 ml of toluene was stirred at 120° C. for 2½ hours and was then evaporated to dryness under reduced pressure. The residue was crystallized from isopropyl ether, was cooled and filtered. The product was dried to obtain 900 mg of (1R,cis)2,2-dimethyl-3-[Z-2-(isopropoxycarbonyl)-ethenyl]-cyclopropane-carboxylic acid melting at 98° C.

STEP D:
(S)α-cyano-3-phenoxy-benzyl(1R,cis)2,2-dimethyl-3-[Z-2-(isopropoxycarbonyl)-ethenyl]-cyclopropane-carboxylate Using the procedure of Step D of Example 1, 900 mg of the product of Step C and 900 mg of (S)α-cyano-3-phenoxybenzyl alcohol were reacted to obtain 1.8 g of raw product which was chromatographed over silica gel. Elution with a 9–1 cyclohexane-ethyl acetate mixture yielded 1.2 g of (S)α-cyano-3-phenoxy-benzyl(1R,cis)2,2-dimethyl-3-[Z-2-(isopropoxycarbonyl)-ethenyl]-cyclopropane-carboxylate with a specific rotation of $[\alpha]_D^{20} = +54° \pm 2°$ (c=0.4% in benzene).

NMR Spectrum (deuterochloroform): Peaks at 1.25 and 1.27 ppm (hydrogens of geminal methyls); at 1.92–2.05 ppm (1-hydrogen of cyclopropane); at 3.25–3.39 ppm and 3.42–3.56 ppm (3-hydrogen of cyclopropane); at 6.3 ppm (hydrogen on carbon attached to —CN); at 5.8–6 ppm

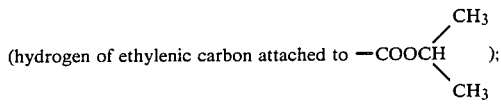

(hydrogen of ethylenic carbon attached to —COOCH(CH$_3$)$_2$);

at 6.35–6.51 ppm and 6.55–6.71 ppm (hydrogen of branched ethylenic carbon attached to cyclopropane); at 5.08 ppm (hydrogen of isopropyl); at 1.23–1.34 ppm (hydrogen of methyls of isopropyl).

EXAMPLE 6

(S)α-cyano-3-phenoxy-benzyl(1R,cis)2,2-dimethyl-3-[Z-2-(tert.-butoxycarbonyl)-ethenyl]-cyclopropane-carboxylate

STEP A:
Tert.-butyl(1R,cis)2,2-dimethyl-3-[2,2,2-trichloroethoxycarbonyl-ethynyl]-cyclopropane-carboxylate A mixture of 6.2 g of dicyclohexylcarbodiimide, 7.15 g of tert.-butyl(1R,cis)2,2-dimethyl-3-(2-carboxyethynyl)-cyclopropane-carboxylate, 80 mg of dimethylaminopyridine and 35 ml of methylene chloride was stirred for 10 minutes and 4.5 g of 2,2,2-trichloroethanol were added thereto. The mixture was stirred for one hour and was filtered and the filtrate was washed with N hydrochloric acid and then with water until the wash water was neutral, dried and evaporated to dryness. The 14 g of oil residue were chromatographed over silica gel and eluted with a 97–3 benzeneethyl acetate mixture to obtain 9 g of tert.-butyl(1R,cis)2,2-dimethyl-3-[2,2,2-trichloroethoxycarbonyl-ethynyl]-cyclopropane-carboxylate melting at 70°–71° C.

STEP B:
(1R,cis)2,2-dimethyl-3-[2,2,2-trichloroethoxycarbonyl-ethynyl]-cyclopropane-carboxylic acid A mixture of 11.4 g of the product of Step A, 120 ml of toluene and 300 mg of p-toluene sulfonic acid was refluxed for one hour and was cooled to room temperature. The mixture was washed with water, dried and evaporated to dryness under reduced pressure to obtain 9.5 g of (1R,cis)2,2-dimethyl-3-[2,2,2-trichloroethoxycarbonyl-ethynyl]-cyclopropane-carboxylic acid which used as is for the next step.

STEP C:
(S)α-cyano-3-phenoxy-benzyl(1R,cis)2,2-dimethyl-3-[2,2,2-trichloroethoxycarbonyl-ethynyl]-cyclopropane-carboxylate 6.2 g of dicyclohexylcarbodiimide were added to a mixture of 9.5 g of the product of Step B, 30 ml of methylene chloride and 3 ml of pyridine and after stirring for 30 minutes, 6.8 g of (S)α-cyano-3-phenoxy-benzyl alcohol were added to the mixture. The mixture was stirred for 90 minutes and was filtered and the filtrate was washed with N hydrochloric acid and then with water until the wash water was neutral, dried and evaporated to dryness. The 16.3 g of oil residue were chromatographed over silica gel and eluted with a 97–3 benzene-ethyl acetate mixture to obtain 12 g of (S)α-cyano-3-phenoxy-benzyl(1R,cis)2,2-dimethyl-3-(2,2,2- trichloroethoxycarbonyl-ethynyl]-cyclopropane-carboxylate melting at 101° C.

STEP D:
(S)α-cyano-3-phenoxy-benzyl(1R,cis)2,2-dimethyl-3-(2-carboxyethynyl)-cyclopropane-carboxylate 5.9 g of powdered zinc were added to a solution of 6.5 g of the product of Step C, 23.4 ml of acetic acid and 2.6 ml of water and the mixture was stirred for one hour and was filtered. The filtrate was decanted and the organic phase was washed with water. The combined aqueous phases were extracted with methylene chloride and the combined organic phases were dried, filtered and evaporated to dryness to obtain 4.7 g of crude (S)α-cyano-3-phenoxy-benzyl(1R,cis)2,2-dimethyl-3-(2-carboxyethynyl)-cyclopropane-carboxylate used as is for the next step.

STEP E:
(S)α-cyano-3-phenoxy-benzyl(1R,cis)2,2-dimethyl-3-[ΔZ-2-carboxyethenyl]-cyclopropane-carboxylate A mixture of 4.7 g of the product of Step D, 45 ml of ethyl acetate, 500 mg of 10% palladium hydroxide on barium sulfate and 6.5 ml of quinoline was hydrogenated and the mixture was filtered. The filtrate was washed with N hydrochloric acid, with water until the wash water was neutral, dried and evaporated to dryness. The 5.1 g of oil residue were chromatographed over silica gel and eluted with a 70–30–1 hexane-ethyl acetate-acetic acid mixture to obtain 3.8 g of (S)α-cyano-3-phenoxy-benzyl(1R,cis)2,2-dimethyl-3-[ΔZ-2-carboxyethenyl]-cyclopropane-carboxylate which was used as is for the next step.

STEP F:
(S)α-cyano-3-phenoxy-benzyl(1R,cis)2,2-dimethyl-3-[Z-2-tert.butylcarbonylethenyl]-cyclopropane-carboxylate A mixture of 1.2 g of the product of Step E, 6 ml of ethyl acetate and 1.2 g of O-tert.-butyl-N,N'-diisopropylurea was stirred at room temperature for 16 hours and was filtered. The filtrate was evaporated to dryness and the 1.55 g of oil residue were chromatographed over silica gel and eluted with benzene to obtain 600 mg of (S)α-cyano-3-phenoxy-benzyl(1R,cis)2,2-dimethyl-3-[Z-2-tert.-butylcarbonylethenyl]-cyclopropane-carboxylate melting at 89° C. and having a specific rotation of $[\alpha]_D^{20} = +61.5° \pm 2°$ (c=0.5% in benzene).

NMR Spectrum (deuterochloroform): Peaks at 1.9–2.04 ppm (1-hydrogen of cyclopropane); at 3.22 to 3.52 ppm (3-hydrogen of cyclopropane); at 1.23 ppm (hydrogens of geminal methyls); at 6.3 ppm (hydrogen on carbon attached to —CN); at 6.24 to 6.6 ppm (hydrogen of 1-carbon of ethenyl); at 5.7 to 5.9 ppm (hydrogen of 2-carbon of ethenyl); at 1.5 ppm (hydrogens of tert.-butyl).

EXAMPLE 7
(S)α-cyano-3-phenoxy-benzyl(1R,cis)2,2-dimethyl-3-[Z-2-(n-butoxycarbonyl)-ethenyl]-cyclopropane-carboxylate

STEP A:
Tert.-butyl(1R,cis)2,2-dimethyl-3-(n-butoxycarbonylethynyl)-cyclopropane-carboxylate 3.4 g of dicyclohexylcarbodiimide were added to a mixture of 4 g of tert.butyl(1R,cis)2,2-dimethyl-3-(2-carboxyethynyl)-cyclopropane-carboxylate, 40 ml of methylene chloride and 6 g of 4-dimethylamino-pyridine and after stirring under an inert atmosphere for 30 minutes, 4 ml of a 1—1 n-butanol-methylene chloride mixture were added to the mixture over 5 minutes. The mixture was stirred at room temperature for 3 hours and was filtered. The filtrate was evaporated to dryness under reduced pressure and the residue was chromatographed over silica gel. Elution with a 9–1 cyclohexane-ethyl acetate mixture yielded 4.7 g of tert.-butyl(1R,cis)2,2-dimethyl-3-(n-butoxycarbonylethynyl)-cyclopropane-carboxylate.

NMR Spectrum (deuterochloroform): Peaks at 1.22 and 1.4 ppm (hydrogens of geminal methyls); at 1.75 ppm (1- and 3-hydrogens of cyclopropane); at 4.15 (t) ppm (1-hydrogen of butoxy); at 1.48 ppm (hydrogens of tert.-butyl).

STEP B:
Tert.-butyl(1R,cis)2,2-dimethyl-3-[Z-2-(n-butoxycarbonyl)ethenyl]-cyclopropane-carboxylate A mixture of 800 mg of palladium hydroxide on barium sulfate and 20 ml of ethyl acetate was stirred under hydrogen for 15 minutes and after 4.7 g of the product of Step A, 0.8 ml of quinoline and 50 ml of ethyl acetate were added to the mixture, the mixture was hydrogenated for 30 minutes. The mixture was filtered and the filtrate was washed with N hydrochloric acid, then with water, dried and evaporated to dryness under reduced pressure. The residue was chromatographed over silica gel and was eluted with a 95–5 cyclohexane-ethyl acetate mixture to obtain 3.4 g of tert.-butyl(1R,cis)2,2-dimethyl-b 3-[Z-2-(n-butoxycarbonyl)-ethenyl]-cyclopropane-carboxylate.

NMR Spectrum (deuterochloroform): Peaks at 1.25 and 1.28 ppm (hydrogens of geminal methyls); at 1.76 and 1.90 ppm (1-hydrogen of cyclopropane); at 2.96 to 3.3 ppm (3-hydrogen of cyclopropane); at 6.45–6.6 ppm and 6.6 to 6.8 ppm (1-hydrogen of allyl); at 5.75 and 5.95 ppm (2-hydrogen of allyl); at 4.12 (t) ppm (1-hydrogen of tert.-butyl); at 1.45 ppm (hydrogens of tert.butyl).

STEP C:
(1R,cis)2,2-dimethyl-3-[Z-2-(n-butoxycarbonyl)ethyenyl]-cyclopropane-carboxylic acid A mixture of 3.3 g of the product of Step B, 350 mg of p-toluene sulfonic acid and 40 ml of toluene was stirred at reflux until isobutylene evolution ceased (about 40 minutes) and was then evaporated to dryness under reduced pressure. The residue was chromatographed over silica gel and was eluted with a 75–25–1 cyclohexane-ethyl acetate-acetic acid mixture to obtain 2 g of (1R,cis)2,2-dimethyl-3-[Z-2-(n-butoxycarbonyl)-ethenyl]-cyclopropane-carboxylic acid.

NMR Spectrum (deuterochloroform): Peaks at 1.26 and 1.3 ppm (hydrogens of geminal methyls); at 1.85–1.99 ppm (1-hydrogen of cyclopropane); at 3.13 to 3.47 ppm (3-hydrogen of cyclopropane); at 6.4–6.57 ppm and 6.59–6.75 ppm (1-hydrogen of allyl); at 5.8–5.99 ppm (2-hydrogen of allyl).

STEP D:
(S)α-cyano-3-phenoxy-benzyl(1R,cis)2,2-dimethyl-3-[Z-2-(n-butoxycarbonyl)-ethenyl]-cyclopropane-carboxylate 1.7 g of dicylohexylcarbodiimide were added with stirring under an inert atmosphere to a mixture of 2 g of the product of Step C, 20 ml of methylene chloride and 1.1 ml of pyridine and the mixture was stirred for 30 minutes after which 3 ml of a solution of 2 g of (S)α-cyano-3-phenoxybenzyl alcohol in methylene chloride were added thereto. The mixture was stirred for 16 hours at room temperature and was then filtered. The filtrate was evaporated to dryness under reduced pressure and the residue was chromatographed over silica gel. Elution with an 8-2 n-hexane-isopropyl ether mixture yielded 3.1 g of (S)α-cyano-3-phenoxy-benzyl(1R,cis)2,2-dimethyl-3-[Z-2-(n-butoxycarbonyl)-ethenyl]-cyclopropanecarboxylate with a specific rotation of $[\alpha]_D^{20} = +51° \pm 2°$ (c=0.4% in benzene).

NMR Spectrum (deuterochloroform): Peaks at 1.25-1.27 ppm (hydrogens of geminal methyls); at 1.92-2.07 ppm (1-hydrogen of cyclopropane); at 3.22-3.37-3.53 ppm (3-hydrogen of cyclopropane); at 6.5 (t) ppm (1-hydrogen of allyl); at 5.8-5.85 ppm (2-hydrogen of allyl); at 6.35 ppm (hydrogen on carbon attached to —CN).

EXAMPLE 8

(S)α-cyano-3-phenoxy-benzyl(1R,cis)2,2-dimethyl-3-[Z-2-(pentyloxycarbonyl)-ethenyl]-cyclopropane-carboxylate

STEP A:

Tert.-butyl(1R,cis)2,2-dimethyl-3-[pentyloxycarbonylethynyl]-cyclopropane-carboxylate Using the procedure of Step A of Example 7, 3 g of tert.-butyl(1R,cis)2,2-dimethyl-3-(2-carboxyethynyl)-cyclopropane-carboxylate and 2 ml of n-amyl alcohol were reacted and the residue was chromatographed over silica gel. Elution with an 8-2 hexane-isopropyl ether mixture yielded 2.7 g of tert.-butyl(1R,cis)2,2-dimethyl-3-[pentyloxycarbonylethynyl]cyclopropane-carboxylate.

STEP B:

(1R,cis)2,2-dimethyl-3-(pentyloxycarbonyl-ethynyl)cyclopropane-carboxylic acid

A mixture of 5.24 g of the product of Step A, 50 ml of toluene and 250 mg of p-toluene sulfonic acid was refluxed until gas evolution ceased and was then evaporated to dryness under reduced pressure to obtain 4.8 g of crude (1R,cis)2,2-dimethyl-3-(pentyloxycarbonyl-ethynyl)-cyclopropane-carboxylic acid which was used as is for the next step.

STEP C:

(1R,cis)2,2-dimethyl-3-[Z-2-(pentyloxycarbonyl)ethenyl]-cyclopropane-carboxylic acid A mixture of 4.8 g of the product of Step B, 50 ml of ethyl acetate, 1 ml of quinoline, 1 g of 10% palladium hydroxide on barium sulfate in 50 ml of ethyl acetate was hydrogenated and the mixture was filtered. The filtrate was washed with N hydrochloric acid, then with water, dried and evaporated to dryness under reduced pressure. The residue was chromatographed over silica gel and was eluted with a 70-30-1 cyclohexane-ethyl acetate-acetic acid mixture to obtain 3 g of (1R,cis)2,2-dimethyl-3-[Z-2-(pentyloxycarbonyl)ethenyl]-cyclopropane-carboxylic acid.

NMR Spectrum (deuterochloroform): Peaks at 1.3 and 1.32 ppm (hydrogens of geminal methyls); at 1.85-1.99 ppm (1-hydrogen of cyclopropane); at 3.15-3.45 ppm (3-hydrogen of cyclopropane); at 6.4 to 6.75 ppm (1-hydrogen of allyl); at 7.58-7.96 ppm (2-hydrogen of allyl).

STEP D:

(S)α-cyano-3-phenoxy-benzyl(1R,cis)2,2-dimethyl-3-[Z-2-(pentyloxycarbonyl)-ethenyl]-cyclopropane-carboxylate Using the procedure of Step D of Example 7, 3.05 g of the product of Step C, 1.5 ml of pyridine, 2.4 g of dicyclohexylcarbodiiumide and 2.7 g of (S)α-cyano-3-phenoxybenzyl alcohol in 20 ml of methylene chloride were reacted and the residue was chromatographed over silica gel. Elution with a 9-1 hexane-ethyl acetate mixture yielded 3.5 g of (S)α-cyano-3-phenoxy-benzyl(1R,cis)2,2-dimethyl-3-[Z-2-(pentyloxycarbonyl)-ethenyl]-cyclopropane-carboxylate.

NMR Spectrum (deuterochloroform): Peaks at 1.25-1.27 ppm (hydrogens of geminal methyls); at 1.92-2.07 ppm (1-hydrogen of cyclopropane); at 3.37 (t) ppm (3-hydrogen of cyclopropane); at 6.3-6.5 ppm and 6.53-6.7 ppm (1-hydrogen of allyl); at 5.8-6 ppm (2-hydrogen of allyl); at 6.3 ppm (hydrogen on carbon attached to —CN); at 6.9t 7.6 ppm (aromatic hydrogens).

EXAMPLE 9

(S)α-cyano-3-phenoxy-benzyl(1R,cis)2,2-dimethyl-3-[Z-2({RS}1-methyl-propyloxycarbonyl)-ethenyl]-cyclopropane-carboxylate STEP A: Tert.-butyl(1R,cis)2,2-dimethyl-3-[(RS)1-methylpropyloxycarbonyl-ethynyl]-cyclopropane-carboxylate Using the procedure of Step A of Example 7, 2 ml of 1-methyl-propyl alcohol were reacted and the residue was chromatographed over silica gel. Elution with an 8-2 n-hexane-isopropyl ether mixture yielded of 3.5 g of tert.-butyl(1R,cis)2,2-dimethyl-3-[(RS)1-methyl-propyloxycarbonyl-ethynyl]cyclopropane-carboxylate.

NMR Spectrum (deuterochloroform): Peaks at 1.2-1.4 ppm (hydrogens of geminal methyls); at 1.73 ppm (1- and 3-hydrogens of cyclopropane); at 4.92 ppm (1-hydrogen of propyl).

STEP B:

Tert.-butyl(1R,cis)2,2dimethyl-3-[Z-2-({RS}1-methyl-propyloxycarbonyl)-ethenyl]-cyclopropane-carboxylate Using the procedure of Step B of Example 7, 3 g of the product of Step A were hydrogenated and the residue was chromatographed over silica gel. Elution with a 9-1 n-hexane-isopropyl ether yielded 2.5 g of tert.-butyl(1R,cis)2,2-dimethyl-3-[Z-2-({RS}1-methyl-propyloxycarbonyl)ethenyl]-cyclopropane-carboxylate.

STEP C:

(1R,cis)2,2-dimethyl-3-[Z-2-({RS}1-methyl-propyl-oxycarbonyl)-ethenyl]-cyclopropane-carboxylic acid Using the procedure of Step C of Example 7, 3 g of the product of Step B were reacted and the residue was chromatographed over silica gel. Elution with a 70-3-0-1 cyclopropane-ethyl acetate-acetic acid mixture yielded 1.85 g of (1R,cis)2,2-dimethyl-3-[Z-2-({RS}1-methyl-propyl-oxycarbonyl)ethenyl]-cyclopropane-carboxylic acid.

IR Spectrum (chloroform): Absorption at 3510 cm$^{-1}$ (acid —OH); at 1735 cm$^{-1}$

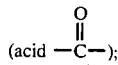
(acid —C—);

at 1710–1700 cm$^{-1}$ (ester); at 1637 cm$^{-1}$ (conjugated C=C); at 1381 cm$^{-1}$ (gem. dimethyls).

STEP D:
(S)α-cyano-3-phenoxy-benzyl(1R,cis)2,2-dimethyl-3-[Z-2-({RS}1-methyl-propyloxycarbonyl)-ethenyl]-cyclopropanecarboxylate Using the procedure of Step D of Example 7, 1.83 g of the product of Step C were reacted to obtain 2.6 g of (S)α-cyano-3-phenoxy-benzyl(1R,cis)2,2-dimethyl-3-[Z-2-({RS}1-methyl-propyloxycarbonyl)-ethenyl]-cyclopropane-carboxylate with a specific rotation of $[\alpha]_D^{20} = +48° \pm 2.5°$ (c=0.5% in benzene).

NMR Spectrum (deuterochloroform): Peaks at 1.22–1.23 ppm (hydrogens of geminal methyls); at 1.88–2.02 ppm (1-hydrogen of cyclopropane); at 3.21 to 3.5 ppm (3-hydrogen of cyclopropane); at 6.35 to 6.68 ppm (1-hydrogen of allyl); at 5.8 to 6 ppm (2-hydrogen of allyl); at 4.92 (m) ppm (1-hydrogen of propyl); at 6.35 ppm (hydrogen on carbon attached to —CN).

EXAMPLE 10

(S)α-cyano-3-phenoxy-benzyl(1R,cis)2,2-dimethyl-3-[Z-2-(isobutoxy-carbonyl)ethenyl]-cyclopropane-carboxylate STEP A:
Tert.-butyl(1R,cis)2,2-dimethyl-3-(isobutoxy-carbonyl-ethynyl)-cyclopropane-carboxylate Using the procedure of Step A of Example 7, 2 ml of isobutyl alcohol were reacted to obtain 4.6 g of tert.-butyl(1R,cis)2,2-dimethyl-3-(isobutoxy-carbonyl-ethynyl)-cyclopropane-carboxylate.

NMR Spectrum (deuterochloroform): Peaks at 1.22–1.4 ppm (hydrogens of geminal methyls); at 3.88–4 ppm (1-hydrogen of isobutyl).

STEP B:
(1R,cis)2,2-dimethyl-3-[isobutoxycarbonyl-ethynyl]cyclopropane-carboxylic acid A mixture of 4.6 g of the product of Step A, 450 mg of p-toluene sulfonic acid and 50 ml of toluene was refluxed for 45 minutes and was evaporated to dryness under reduced pressure. The residue was chromatographed over silica gel and was eluted with a 70–30–1 cyclohexane-ethyl acetate-acetic acid mixture to obtain 2.9 g of (1R,cis)2,2-dimethyl-3-[isobutoxycarbonyl-ethynyl]-cyclopropane-carboxylic acid.

NMR Spectrum (deuterochloroform): Peaks at 1.25–1.27 ppm (hydrogens of geminal methyls); at ∼1.9 ppm (1- and 3-hydrogens of cyclopropane); at 7.9 ppm (hydrogen of —COOH); at 3.88–4 ppm (1-hydrogen of isobutyl).

STEP C:
(S)α-cyano-3-phenoxy-benzyl(1R,cis)2,2-dimethyl-3-[isobutoxycarbonyl-ethynyl]-cyclopropane-carboxylate Using the procedure of Step D of Example 7, 2.4 g of the product of Step A were reacted and the residue was chromatographed over silica gel. Elution with an 8-2 cyclohexane-ethyl acetate mixture yielded 3.3 g of (S)α-cyano-3-phenoxy-benzyl(1R,cis)2,2-dimethyl-3-[isobutoxycarbonyl-ethynyl]-cyclopropane-carboxylate.

NMR Spectrum (deuterochloroform): Peaks at 1.33–1.23 ppm (hydrogens of geminal methyls); at 1.95 ppm (1- and 3-hydrogens of cyclopropane); at 6.45 ppm (hydrogen on carbon attached to —CN).

STEP D:
(S)α-cyano-phenoxy-benzyl(1R,cis)2,2-dimethyl-3-[Z-2-(isobutoxycarbonyl)-ethenyl]-cyclopropane-carboxylate Using the procedure of Step B of Example 7, 1.4 g of the product of Step C were hydrogenated and the residue was chromatographed over silica gel. Elution with a 8-2 n-hexane-isopropyl ether mixture yielded 1.23 g of (S)α-cyanophenoxy-benzyl(1R,cis)2,2-dimethyl-3-[Z-2-(isobutoxycarbonyl)-ethenyl]-cyclopropane-carboxylate with a specific rotation of $[\alpha]_D^{20} = +57.5° \pm 4°$ (c=0.4% in benzene).

NMR Spectrum (deuterochloroform): Peaks at 1.25 ppm (hydrogens of geminal methyls); at 1.9–2.0 ppm (1-hydrogen of cyclopropane); at 3.2 to 3.5 ppm (3-hydrogen of cyclopropane); at 6.3 to 6.6 ppm (1-hydrogen of allyl); at 5.8–6 ppm (2-hydrogen of allyl); at 6.3 ppm (hydrogen on carbon attached to —CN).

EXAMPLE 11

(S)α-cyano-3-phenoxy-benzyl(1R,cis)2,2-dimethyl-3-[Z-2-(cyclohexyloxycarbonyl)-ethenyl]-cyclopropane-carboxylate STEP A:
Tert.-butyl(1R,cis)2,2-dimethyl-3-(cyclohexyloxycarbonyl-ethynyl)-cyclopropane-carboxylate Using the procedure of Step A of Example 7, 2 ml of cyclohexanol were reacted to obtain 3.67 g of tert.-butyl(1R,cis)2,2-dimethyl-3-(cyclohexyloxycarbonyl-ethynyl)-cyclopropane-carboxylate.

IR Spectrum (chloroform): Absorption at 2225 cm$^{-1}$ (conjugated —C≡C); at 1729 cm$^{-1}$-1700 cm$^{-1}$

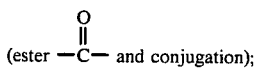
(ester —C— and conjugation);

at 1392 cm$^{-1}$-1380 cm$^{-1}$ (gem. dimethyls); at 1370 cm$^{-1}$ (tert.-butyl).

STEP B:
Tert.-butyl(1R,cis)2,2-dimethyl-3-[Z-2-(cyclo-oxyhexylcarbonyl)-ethenyl]-cyclopropane-carboxylate Using the procedure of Step B of Example 7, 3.67 g of the product of Step A were hydrogenated to obtain 3.4 g of crude tert.-butyl(1R,cis)2,2-dimethyl-3-[Z-2-(cyclohexyl-oxycarbonyl)-ethenyl]-cyclopropane-carboxylate which was used as for the next step.

IR Spectrum (chloroform): Absorption at 1715 cm$^{-1}$ (C=O); at 1634 cm$^{-1}$ (C=C).

Step C:
(1R,cis)2,2-dimethyl-3-[Z-2-(cyclohexyloxycarbonyl)ethenyl]-cyclopropane-carboxylic acid Using the procedure of Step C of Example 7, 3.404 g of the product of Step B were reacted and the residue was chromatographed over silica gel. Elution with a 70–30–1 cyclohexane-ethyl acetate-acetic acid mixture yielded 2.5 g of (1R,cis)2,2-dimethyl-3-[Z-2-(cyclohexyloxycarbonyl)ethenyl]-cyclopropane-carboxylic acid.

IR Spectrum (chloroform): Absorption at 3510 cm$^{-1}$ (acid —OH); at 1735 cm$^{-1}$ (acid C=O); at 1707 cm$^{-1}$ (ester); at 1380 cm$^{-1}$ (gem. dimethyls); at 1638 cm$^{-1}$ (—C=C—).

STEP D:

(S)α-cyano-3-phenoxy-benzyl(1R,cis)2,2-dimethyl-3-[Z-2-(cyclohexyloxycarbonyl)-ethenyl]-cyclopropane-carboxylate Using the procedure of Step D in Example 7, 2.5 g of the product of Step C and 2.2 g of (S)α-cyano-3-phenoxybenzyl alcohol were reacted and the product was chromatographed over silica gel. Elution with a 9–1 hexane-ether mixture yielded 1.883 g of (S)α-cyano-3-phenoxy-benzyl(1R,cis)2,2-dimethyl-3-[Z-2-(cyclohexyloxycarbonyl)-ethenyl]-cyclopropane-carboxylate with a specific rotation of $[\alpha]_D^{20} = +41° \pm 2.5°$ (c=0.5% in chloroform).

NMR Spectrum (deuterochloroform): Peaks at 1.26 ppm (hydrogens of geminal methyls); at 1.92–2.05 ppm (1-hydrogen of cyclopropane); at 3.23–3.55 ppm (3-hydrogen of cyclopropane); at 6.3 to 6.6 ppm (1-hydrogen of allyl); at 5.8–5.99 ppm (2-hydrogen of allyl); at 6.3 ppm (hydrogen on carbon attached to —CN); at 4.8 ppm (1-hydrogen of cyclohexyl).

EXAMPLE 12

(S)α-cyano-3-phenoxy-benzyl(1R,cis)2,2-dimethyl-3-[Z-2-cyclopropylmethoxycarbonyl)-ethenyl]-cyclopropane-carboxylate

STEP A:

(S)α-cyano-phenoxy-benzyl(1R,cis)2,2-dimethyl-3-(cyclopropylmethoxycarbonyl-ethynyl)-cyclopropane-carboxylate Using the procedure of Step A of Example 7, 1.4 g of (S)α-cyano-3-phenoxy-benzyl(1R,cis)2,2-dimethyl-3-(2-carboxyethynyl)-cyclopropane-carboxylate and 0.3 ml of cyclopropylcarbinol were reacted and the product was chromatographed over silica gel. Elution with an 8–2 cyclohexane-ethyl acetate mixture yielded 1.5 g of (S)α-cyano-3-phenoxybenzyl(1R,cis)2,2-dimethyl-3-(cyclopropylmethoxycarbonylethynyl)-cyclopropane-carboxylate melting at 72° C.

IR Spectrum (chloroform): Absorption at 2235 cm$^{-1}$ (conjugated —C≡C—); at 1754 cm$^{-1}$ (ester C=O); at 1704 cm$^{-1}$ (conj. ester); at 1390 and 1380 cm$^{-1}$ (gem. dimethyls).

STEP B:

(S)α-cyano-3-phenoxy-benzyl(1R,cis)2,2-dimethyl-3-[Z-2-(cyclopropylmethoxycarbonyl)-ethynyl]-cyclopropane-carboxylate Using the procedure of Step B of Example 7, 1.5 g of the product of Step A were hydrogenated and the product was chromatographed over silica gel. Elution with an 8–2 n-hexane-isopropyl ether mixture yielded 1.2 g of (S)α-cyano-3-phenoxy-benzyl(1R,cis)2,2-dimethyl-3-[Z-2-(cyclopropyloxycarbonyl)-ethenyl]-cyclopropane-carboxylate with a specific rotation of $[\alpha]_D^{20} = +48.5° \pm 2.5°$ (c=0.5% in benzene).

NMR Spectrum (deuterochloroform): Peaks at 1.27 ppm (hydrogens of geminal methyls); at 1.92–2.06 ppm (1-hydrogen of cyclopropane); at 3.2 to 3.5 ppm (3-hydrogen of cyclopropane); at 6.3 to 6.75 ppm (1-hydrogen of allyl); at 5.9–6 ppm (2-hydrogen of allyl); at 6.37 ppm (hydrogen on carbon attached to —CN).

EXAMPLE 13

(S)α-cyano-3-phenoxy-benzyl(1R,cis)2,2-dimethyl-3-[Z-2-(cyclobutoxycarbonyl)-ethenyl]-cyclopropane-carboxylate

STEP A:

Tert.-butyl(1R,cis)2,2-dimethyl-3-[Z-2-(cyclobutoxycarbonyl)-ethenyl]-cyclopropane-carboxylate 1.7 ml of cyclobutanol were added to a solution of 4 g of tert.-butyl(1R,cis)2,2-dimethyl-3-[Z-2-carboxyethenyl]-cyclopropane-carboxylate in 20 ml of methylene chloride and 3.45 g of dicyclohexylcarbodiimide and a solution of 28 mg of 4-dimethylamino-pyridine in 20 ml of methylene chloride were added thereto at 0° to 5° C. with stirring. The mixture was stirred for 2 hours at 5° C. and 2 hours at room temperature and was then filtered. The filtrate was evaporated to dryness under reduced pressure and the residue was chromatographed over silica gel. Elution with a 9–1 n-hexane-isopropyl ether mixture yielded 2.3 g of tert.-butyl(1R,cis)2,2-dimethyl-3-[Z-2-(cyclobutoxycarbonyl)-ethenyl]cyclopropane-carboxylate.

NMR Spectrum (deuterochloroform): Peaks at 1.23–1.26 ppm (hydrogens of geminal methyls); at 1.77–1.9 ppm (1-hydrogen of cyclopropane); at 2.95 to 3.28 ppm (3-hydrogen of cyclopropane); at 6.4 to 6.8 ppm (1-hydrogen of allyl); at 5.7–5.9 ppm (2-hydrogen of allyl); at 5 ppm (1-hydrogen of cyclobutyl).

STEP B:

(1R,cis)2,2-dimethyl-3-[Z-2-(cyclobutyoxycarbonyl)ethenyl]-cyclopropane-carboxylic acid A mixture of 2.3 g of the product of Step A, 25 ml of toluene and 250 mg of p-toluene sulfonic acid was heated to reflux and was cooled and stirred at 0° to 5° C. for 2 hours. The mixture was filtered and the filtrate was evaporated to dryness under reduced pressure to obtain 1.8 g of (1R,cis)2,2-dimethyl-3-[Z-2-(cyclobutoxycarbonyl)-ethenyl]-cyclopropane-carboxylic acid.

IR Spectrum (chloroform): Absorption at 3500 cm$^{-1}$ (acid OH); at 1733 cm$^{-1}$ (acid C=O); at 1702 cm$^{-1}$ (conj. ester); at 1390 and 1380 cm$^{-1}$ (gem. dimethyls).

STEP C:

(S)α-cyano-3-phenoxy-benzyl(1R,cis)2,2-dimethyl-3-[Z-2-(cyclobutoxycarbonyl)-ethenyl]-cyclopropane-carboxylate Using the procedure of Step A above, 1.8 g of the acid of Step B and 2 g of (S)α-cyano-3-phenoxy-benzyl alcohol were reacted and the product was chromatographed over silica gel. Elution with a 9–1 cyclohexane-ethyl acetate mixture and then with an 8–2 n-hexane-isopropyl ether mixture yielded 3.0 g of (S)α-cyano-3-phenoxy-benzyl(1R,cis)2,2-dimethyl-3-[Z-2-(cyclobutoxycarbonyl)-ethenyl]-cyclopropane-carboxylate with a specific rotation of $[\alpha]_D^{20} = +45.5° \pm 2°$ (c=0.6% in chloroform).

NMR Spectrum (deuterochloroform): 1.25–1.26 ppm (hydrogens of geminal methyls); at 3.4 ppm (3-hydrogen of cyclopropane); at 6.5 to 6.7 ppm (1-hydrogen of allyl); at 5.8–6.0 ppm (2-hydrogen of allyl); at 5.1 ppm (1-hydrogen of cyclobutyl); at 6.4 ppm (hydrogen or carbon attached to —CN).

EXAMPLE 14

(S)α-cyano-3-phenoxy-benzyl(1R,cis)2,2-dimethyl-3-[Z-2-cyclopentyloxycarbonyl)-ethenyl]-cyclopropane-carboxylate

STEP A:
Tert.-butyl(1R,cis)2,2-dimethyl-3-[2-cyclopentyloxycarbonyl)-ethynyl]-cyclopropane-carboxylate Using the procedure of Step A of Example 7, 5.8 g of tert.-butyl(1R,cis)2,2-dimethyl-3-[2-carboxyethynyl]cyclopropane-carboxylate and 2.2 ml of cyclopentanol were reacted and the residue was chromatographed over silica gel. Elution with a 7–3 n-hexane-isopropyl ether mixture yielded 4.8 g of tert.-butyl(1R,cis)2,2-dimethyl-3-[2-cyclopentyloxycarbonyl)-ethynyl]-cyclopropane-carboxylate.

IR Spectrum (chloroform): Absence of OH; absorption at 2230 cm$^{-1}$ (conj. C≡C); at 1727 cm$^{-1}$-1695 cm$^{-1}$ (C=O); at 1395 cm$^{-1}$ and 1380 cm$^{-1}$ (gem. dimethyls); at 1372 cm$^{-1}$ (tert.-butyl).

STEP B:
(1R,cis)2,2-dimethyl-3-[2-cyclopentyloxycarbonylethynyl]-cyclopropane-carboxylic acid A mixture of 4.8 g of the product of Step A, 500 mg of p-toluene sulfonic acid and 50 ml of toluene was refluxed for 10 minutes and was cooled and washed with water, dried and evaporated to dryness under reduced pressure to obtain 3.6 g of (1R,cis)2,2-dimethyl-3-[2-cyclopentyloxycarbonyl-ethynyl]-cyclopropane-carboxylic acid used as is for the next step.

STEP C:
(S)α-cyano-3-phenoxy-benzyl(1R,cis)2,2-dimethyl-3-[2-(cyclopentyloxycarbonyl)-ethynyl]-cyclopropane-carboxylate 2.96 g of dicyclohexylcarbodiimide were added at 0° C. to a stirred mixture of 3.6 g of the product of Step B, 30 ml of methylene chloride and 30 mg of 4-dimethylaminopyridine followed by the addition of a solution of 3.3 g of (S)α-cyano-3-phenoxy-benzyl alcohol in 10 ml of methylene chloride. The mixture was stirred at 0° C. for 5 minutes and at 20°–25° C. for 3 hours and was filtered. The filtrate was evaporated to dryness under reduced pressure and the residue was chromatographed over silica gel. Elution with a cyclohexane-ethyl acetate mixture yielded 4.5 g of (S)α-cyano-3-phenoxybenzyl(1R,cis)2,2-dimethyl-3-[2-(cyclopentyloxycarbonyl)ethynyl]-cyclopropane-carboxylate with a melting point of =72° C.

NMR Spectrum (deuterochloroform): Peaks at 1.25 and 1.37 ppm (hydrogens of geminal methyls); at 1.95 ppm (1- and 3-hydrogens of cyclopropane); at 6.65 ppm (hydrogen on carbon attached to —CN); at 5.25 ppm (1-hydrogen of cyclopentyl).

STEP D:
(S)α-cyano-3-phenoxy-benzyl(1R,cis)2,2-dimethyl-3-[Z-2-(cyclopentyloxycarbonyl)-ethenyl]-cyclopropane-carboxylate Using the procedure of Step D of Example 10, 3 g of the product of Step C were reacted and the residue was chromatographed over silica gel. Elution with an 85–15 cyclohexane-ethyl acetate mixture yielded 2.2 g of (S)α-cyano-3-phenoxy-benzyl(1R,cis)2,2-dimethyl-3-[Z-2-(cyclopentyloxycarboxyl)-ethenyl]-cyclopropane-carboxylate with a specific rotation of $[\alpha]_D^{20} = +43.5° \pm 2.5°$ (c=0.5% in benzene).

NMR Spectrum (deuterochloroform): Peaks at 1.27–1.28 ppm (hydrogens of gem, dimethyls); at 1.92–2.06 ppm (1-hydrogen of cyclopropane); at 3.25 to 3.57 ppm (3-hydrogen of cyclopropane); at 6.38 to 6.7 ppm (1-hydrogen of allyl); at 5.83–6.0 ppm (2-hydrogen of allyl); at 5.25 ppm (1-hydrogen of cyclopentyl); at 6.38 ppm (hydrogen on carbon attached —CN).

EXAMPLE 15

(S)α-cyano-3-phenoxy-benzyl(1R,cis)2,2-dimethyl-3-[Z-2-(tert.-amyloxycarbonyl)-ethenyl]-cyclopropane-carboxylate

STEP A:
(S)α-cyano-3-phenoxy-benzyl(1R,cis)2,2-dimethyl-3-[2tert.-amyloxycarbonyl-ethynyl]-cyclopropane-carboxylate 82 mg of 4-dimethylamino-pyridine were added with stirring at 5° C. to a mixture of 2.5 g of (S)α-cyano-3-phenoxybenzyl(1R,cis)2,2-dimethyl-3-[2-carboxycarbonylethynyl]-cyclopropane-carboxylate, 12.5 ml of methylene chloride and 2.5 ml of tert.-amyl alcohol followed by the addition of 1.55 g of dicyclohexylcarbodiimide. The mixture was stirred at 20° C. for 4½ hours and was cooled to 0° C. and filtered. The filtrate was evaporated to dryness under reduced pressure and was chromatographed over silica gel. Elution with an 8–2 cyclohexane-ethyl acetate mixture yielded 1.35 g of (S)α-cyano-3-phenoxy-benzyl(1R,cis)2,2-dimethyl-3-[2-tert.-amyloxycarbonyl-ethynyl]-cyclopropane-carboxylate.

IR Spectrum (chloroform): Absorption at 2235 cm$^{-1}$ (—C≡C); at 1756 cm$^{-1}$ (ester carbonyl); at 1699 cm$^{-1}$ (conj. ester); at 1589 cm$^{-1}$ and 1489 cm$^{-1}$ (aromatics); at 1392 cm$^{-1}$ and 1382 cm$^{-1}$ (gem. dimethyls).

STEP B:
(S)α-cyano-3-phenoxy-benzyl(1R,cis)2,2-dimethyl-3-[Z-2-(tert.-amyloxycarbonyl)-ethenyl]-cyclopropane-carboxylate A mixture of 1.34 g of the product of Step A, 220 mg of 10% palladium hydroxide on barium sulfate, 20 ml of ethyl acetate and 0.25 ml of quinoline was hydrogenated for 30 minutes and was filtered. The filtrate was evaporated to dryness under reduced pressure and the residue was chromatographed over silica gel. Elution with a 9:1 cyclohexane-ethyl acetate mixture yielded 1.05 g of (S)α-cyano-3-phenoxy-benzyl(1R,cis)2,2-dimethyl-3-[Z-2-(tert.-amyloxycarbonyl)-ethenyl]cyclopropane-carboxylate with a specific rotation of $[\alpha]_D^{20} = +63.5° \pm 2.5°$ (c=0.7% in chloroform).

NMR Spectrum (deuterochloroform): Peaks at 1.26–1.27 ppm (hydrogens of geminal methyls); at 6.28–6.45 ppm and 6.48–6.65 ppm (1-hydrogen of ethyl); at 5.79–5.82 ppm (2-hydrogen of allyl); at 6.38 ppm (hydrogen on carbon attached to —CN); at 6.98–7.67 ppm (aromatic hydrogens); at 1.48 ppm (hydrogens of 1—CH$_3$ of tert.-amyl); at 0.9 (t) ppm (hydrogen of 3—CH$_3$ of tert.amyl).

EXAMPLE 16

(S)α-cyano-3-phenoxy-benzyl(1R,cis)2,2-dimethyl-3-[Z-2-(1-methylcyclobutyloxycarbonyl)-ethenyl]-cyclopropane-carboxylate

STEP A:

(S)α-cyano-3-phenoxy-benzyl(1R,cis)2,2-dimethyl-3-[2-(1-methyl-cyclobutoxycarbonyl)-ethynyl]-cyclopropane-carboxylate Using the procedure of Step A of Example 15, 3.9 g of (S)α-cyano-3-phenoxy-benzyl(1R,cis)2,2-dimethyl-3-(2-carboxyethynyl)-cyclopropane-carboxylate and 4.3 g of 1-methylcyclobutanol were reacted with stirring at 20° C. for 18 hours. The product was chromatographed over silica gel and was eluted with an 85-15 cyclohexane-ethyl acetate mixture to obtain 2.7 g of (S)α-cyano-3-phenoxy-benzyl(1R,cis)2,2-dimethyl-3-[2-(1-methyl-cyclobutoxycarbonyl)-ethynyl]-cyclopropane-carboxylate melting at 76° C.

NMR Spectrum (deuterochloroform): Peaks at 1.23-1.35 ppm (hydrogens of geminal methyls); at 1.93 ppm (1- and 3-hydrogens of cyclopropane); at 1.58 ppm (hydrogen of 1—CH₃ of cyclobutyl); at 6.55 ppm (hydrogen on carbon attached to —CN).

STEP B:

(S)α-cyano-3-phenoxy-benzyl(1R,cis)2,2-dimethyl-3-[Z-2-(1-methylcyclobutoxycarbonyl)-ethenyl]-cyclopropane-carboxylate Using the procedure of Step B of Example 15, 2.7 g of the product of Step A were hydrogenated for 15 minutes and the residue was chromatographed over silica gel. Elution with a 95-5 cyclohexane-ethyl acetate mixture yielded 2.38 g of (S)α-cyano-3-phenoxy-benzyl(1R,cis)2,2-dimethyl-3-[Z-2-(1-methylcyclobutoxycarbonyl)-ethenyl]-cyclopropane-carboxylate melting at 78° C.

NMR Spectrum (deuterochloroform): Peaks at 1.27 ppm (hydrogens of geminal methyls); at 3.23 to 3.55 ppm (3-hydrogen of cyclopropane); at 6.23 to 6.68 ppm (1-hydrogen of allyl); at 5.79-5.97 ppm (2-hydrogen of allyl); at 1.6 ppm (hydrogen of 1—CH₃ of cyclobutyl); at 6.38 ppm (hydrogen on carbon attached to —CN); at 6.97 to 7.6 ppm (aromatic hydrogens).

EXAMPLE 17

(S)α-cyano-3-phenoxy-benzyl(1R,cis)2,2-dimethyl-3-[Z-2-(neopentyloxycarbonyl)-ethenyl]-cyclopropane-carboxylate

STEP A:

(S)α-cyano-3-phenoxy-benzyl(1R,cis)2,2-dimethyl-3-[2-neopentyloxycarbonyl-ethynyl]-cyclopropane-carboxylate Using the procedure of Step A of Example 15, 3.89 g of (S)α-cyano-3-phenoxy-benzyl(1R,cis)2,2-dimethyl-3-(2-carboxyethynyl)-cyclopropane-carboxylate and 1 g of neopentyl alcohol were reacted and the mixture was stirred at room temperature for 4 hours and was filtered. The filtrate was washed with N hydrochloric acid, with water, dried and evaporated to dryness under reduced pressure. The residue was chromatographed over silica gel and was eluted with an 8-2 cyclohexane-ethyl acetate mixture to obtain 3.8 g of (S)α-cyano-3-phenoxy-benzyl(1R,cis)2,2-dimethyl-3-[2-neopentyloxycarbonyl-ethynyl]-cyclopropane-carboxylate melting at 67° C.

NMR Spectrum (deuterochloroform): Peaks at 1.25 and 1.36 ppm (hydrogens of geminal methyls); at 1.95 ppm (1- and 3-hydrogens of cyclopropyl); at 3.9 ppm (1-hydrogen of neopentyl); at 0.97 ppm (hydogens of methyls of neopentyl); at 6.53 ppm (hydrogen on carbon attached to —CN).

STEP B:

(S)α-cyano-3-phenoxy-benzyl(1R,cis)2,2-dimethyl-3-[Z-2-(neopentyloxycarbonyl)-ethenyl]-cyclopropane-carboxylate Using the procedure of Step B of Example 15, 2.6 g of the product of Step A were hydrogenated and the filtrate was washed with N hydrochloric acid, with water, dried and evaporated to dryness under reduced pressure. The residue was chromatographed twice over silica gel with elution with an 8-2 cyclohexane-ethyl acetate mixture and then with a 95-5 cyclohexane-ethyl acetate mixture to obtain 2 g of (S)α-cyano-3-phenoxy-benzyl(1R,cis)2,2-dimethyl-3-[Z-2-(neopentyloxycarbonyl-ethenyl]-cyclopropane-carboxylate with a specific rotation of $[\alpha]_D^{20} = +52.5° \pm 2.5°$ (c=0.5% in benzene).

NMR Spectrum (deuterochloroform): Peaks at 1.27-1.275 ppm (hydrogens of geminal methyls); at 1.92-2.07 ppm (1-hydrogen of cyclopropyl); at 3.25 to 3.58 ppm (3-hydrogen or cyclopropane); at 6.4 to 6.75 ppm (1-hydrogen of allyl); at 5.9-6.1 ppm (2-hydrogen of allyl); at 6.4 ppm (hydrogen on carbon attached to —CN); at 3.87 ppm (1-hydrogens of neopentyl); at 0.97 ppm (hydrogens of methyls of neopentyl).

EXAMPLE 18

(S)α-cyano-3-phenoxy-benzyl(1R,cis)2,2-dimethyl-3-[Z-2-(1-methylcyclopentyloxycarbonyl)-ethenyl]-cyclopropane-carboxylate

STEP A:

(S)α-cyano-3-phenoxy-benzyl(1R,cis)2,2-dimethyl-3-[2-(1-methylcyclopentyloxycarbonyl)-ethynyl]-cyclopropanecarboxylate Using the procedure of Step A of Example 15, 3 g of (S)α-cyano-3-phenoxy-benzyl(1R,cis)2,2-dimethyl-3-[2-carboxyethynyl]-cyclopropane-carboxylate and 3 g of 1-methylcyclopentanol were reacted. The residue was chromatographed over silica gel and was eluted with an 8-2 n-hexane-ethyl acetate mixture to obtain 2 g of (S)α-cyano-3-phenoxy-benzyl(1R,cis)2,2-dimethyl-3-[2-(1-methylcyclopentyloxycarbonyl)ethynyl]-cyclopropane-carboxylate.

IR Spectrum (chloroform): Absorption at 2230 cm$^{-1}$ (conjugated —C≡C—); at 1765 cm$^{-1}$ and 1695 cm$^{-1}$ (ester carbonyl and conj. ester); at 1585 and 1485 cm$^{-1}$ (aromatics); at 1390 and 1380 cm$^{-1}$ (gem. dimethyls).

STEP B:

(S)α-cyano-3-phenoxy-benzyl(1R,cis)2,2-dimethyl-3-[Z-2-(1-methylcyclopentyloxycarbonyl)-ethenyl]-cyclopropanecarboxylate Using the procedure of Step B of Example 15, 2 g of the product of Step A were hydrogenated and the residue was chromatographed over silica gel. Elution with a 9-1 n-hexane-ethyl acetate mixture yielded 1.5 g of (S)α-cyano-3-phenoxy-benzyl(1R,cis)2,2-dimethyl-3-[Z-2-(1-methylcyclopentyloxycarbonyl)-ethenyl]-cyclopropane-carboxylate with a specific rotation of $[\alpha]_D^{20} = +61.5° \pm 2.5°$ (c=0.5% in chloroform).

NMR Spectrum (deuterochloroform): Peaks at 1.25-1.26 ppm (hydrogens of geminal methyls); at 1.91-2.05 ppm (1-hydrogen or cyclopropyl); at 3.4 (t)

ppm (3-hydrogen of cyclopropyl); at 6.3 to 6.7 ppm (1-hydrogen of allyl); at 5.8–6 ppm (2-hydrogen of allyl); at 1.61 ppm (hydrogens of 1-methyl of cyclopentyl); at 6.38 ppm (hydrogen on carbon attached to —CN; at 1.67 ppm (hydrogens of cyclopentyl); at 6.9 to 7.6 ppm (aromatic hydrogens).

EXAMPLE 19

(S)α-cyano-3-phenoxy-benzyl(1R,cis)2,2-dimethyl-3-[Z-2-(1-R,S)-cyclopropylethoxycarbonyl)-ethenyl]-cyclopropane-carboxylate Using the procedure of Step A of Example 15, 2 g of (S)α-cyano-3-phenoxy-benzyl(1R,cis)2,2-dimethyl-3-[Z-2-carboxyethenyl]-cyclopropane-carboxylate and 0.8 ml of 1-R,S-cyclopropylethanol were reacted and the mixture was stirred for 3 hours at 12° C. and was evaporated to dryness under reduced pressure. The residue was chromatographed over silica gel and was eluted with an 8–2 n-hexane-ethyl acetate mixture to obtain 0.960 g of (S)α-cyano-3-phenoxy-benzyl(1R,cis)2,2-dimethyl-3-[Z-2-(1-R,S-cyclopropylethoxycarbonyl)-ethenyl]-cyclopropane-carboxylate with a specific rotation of $[\alpha]_D^{20} = +42°$ C.±2.5° (c=0.6% in chloroform).

NMR Spectrum (deuterochloroform): Peaks at 1.25–1.28 ppm (hydrogens of geminal methyls); at 3.25 to 3.58 ppm (3-hydrogen of cyclopropyl); at 1.92–2.06 ppm (1-hydrogen of cyclopropyl); at 6.4 to 6.75 ppm (1-hydrogen of allyl); at 4.43 ppm (1-hydrogen of ethoxy); at 6.4 ppm (hydrogen on carbon attached to —CN); at 1.28–1.38 ppm (2-hydrogens of ethoxy).

EXAMPLE 20

(S)α-cyano-3-phenoxy-benzyl(1R,cis)2,2-dimethyl-3-[Z-2-(2-isopropyl)-propyloxycarbonyl)-ethenyl]-cyclopropane-carboxylate A mixture of 3 g of (S)α-cyano-3-phenoxy-benzyl(1R,cis)2,2-dimethyl-3-[Z-2-carboxy-ethenyl]-cyclopropanecarboxylate in 30 ml of methylene chloride was added to a mixture of 3 ml of 1-dimethylamino-1-chloro-2-methyl-propen-1-yl [J. Org. Chem., Vol. 35 (1970), p. 3970] in 3 ml of methylene chloride and the mixture was stirred at room temperature for 15 minutes. After cooling the mixture to 5° C., 5 ml of 2-isopropyl-propanol were added thereto and the mixture was stirred at room temperature for 16 hours, was washed with water, with aqueous sodium chloride solution, was dried and evaporated to dryness under reduced pressure. The residue was chromatographed over silica gel and was eluted with a 9–1 cyclohexane-ethyl acetate mixture to obtain 2.25 g of (S)α-cyano-3-phenoxy-benzyl (1R,cis)2,2-dimethyl-3-[Z-2-(2-isopropyl-propyloxycarbonyl)-ethenyl]-cyclopropane-carboxylate with a specific rotation of $[\alpha]_D^{20} = +61.5°±2.5°$ (c=0.5% in benzene).

NMR Spectrum (deuterochloroform): Peaks at 1.27 ppm (hydrogens of geminal methyls); at 3.25 to 3.57 ppm (3-hydrogen of cyclopropyl); at 1.90–2.05 ppm (1-hydrogen of cyclopropyl); at 6.3 to 6.6 ppm (1-hydrogen of allyl); at 5.8–5.9 ppm (2-hydrogen of allyl); at 2.28 ppm (2-hydrogen of isopropyl-propanyl); at 6.4 ppm (hydrogen on carbon attached to —CN).

EXAMPLE 21

(S)α-cyano-3-phenoxy-benzyl(1R,cis)2,2-dimethyl-3-[Z-2-(1,1-dimethylallyloxycarbonyl)-ethenyl]-cyclopropane-carboxylate

STEP A:

(S)α-cyano-3-phenoxy-benzyl(1R,cis)2,2-dimethyl-3-[2-(1,1-dimethylallyloxycarbonyl)-ethynyl]-cyclopropane-carboxylate Using the procedure of Step A of Example 15, 2 g of (S)α-cyano-3-phenoxy-benzyl(1R,cis)2,2-dimethyl-3-[2-carboxy-ethynyl]-cyclopropane-carboxylate, 3 ml of 2-methyl-3-buten-2-ol and 150 mg of 4-dimethylamino-pyridine were admixed at 0° C. with 1.06 g of dicyclohexylcarbodiimide in 3 ml of methylene chloride and the mixture was stirred at room temperature for 16 hours. The mixture was evaporated to dryness and the residue was chromatographed over silica gel. Elution with a 9–1 cyclohexane-ethyl acetate mixture yielded 700 mg of (S)α-cyano-3-phenoxy-benzyl(1R,cis)2,2-dimethyl-3-[2-(1,1-dimethylallyloxycarbonyl)-ethynyl]-cyclopropane-carboxylate.

STEP B:

(S)α-cyano-3-phenoxy-benzyl(1R,cis)2,2-dimethyl-3-[Z-2-(1,1-dimethylallyloxycarbonyl)-ethenyl]-cyclopropanecarboxylate Using the procedure of Step B of Example 15, 450 mg of the product of Step A were reacted to obtain 370 mg of (S)α-cyano-3-phenoxy-benzyl(1R,cis)2,2-dimethyl-3-[Z-2-(1,1-dimethylallyloxycarbonyl)-ethenyl]-cyclopropane-carboxylate with a specific rotation of $[\alpha]_D^{20} = +40°$ (c=0.5% in benzene).

NMR Spectrum (deuterochloroform): Peaks at 1.27 ppm (hydrogens of geminal methyls); at 3.25 to 3.6 ppm (3-hydrogen of cyclopropyl); at 1.9–2.04 ppm (1-hydrogen of cyclopropyl); at 6.32–6.68 ppm (1-hydrogen of 3-allyl); at 5.8–6.02 ppm (2-hydrogen of 3-allyl); at 1.57 ppm (hydrogens of 1—CH$_3$ of allyl); at 6 to 6.5 ppm (2-hydrogen of allyl); at 5.03 to 5.37 ppm (3-hydrogen of allyl); at 6.4 ppm (hydrogen on carbon attached to —CN).

EXAMPLE 22

(S)α-cyano-3-phenoxy-benzyl(1R,cis)2,2-dimethyl-3-[Z-2-(cyclopropyloxycarbonyl)-ethenyl]-cyclopropane-carboxylate 0.9 ml of cyclopropanol were added to a mixture of 5.5 g of (S)α-cyano-3-phenoxy-benzyl(1R,cis)2,2-dimethyl-3-[Z-2-carboxy-ethenyl]-cyclopropane-carboxylate in 26 ml of methylene chloride and 1 g of 4-dimethylamino-pyridine and 3 g of dicyclohexylcarbodiimide were added thereto at 0° C. The mixture was stirred at 20° C. for 90 minutes and was filtered. The filtrate was evaporated to dryness under reduced pressure and the residue was chromatographed over silica gel. Elution with an 85–15 cyclohexane-ethyl acetate mixture yielded 3.6 g of (S)α-cyano-3-phenoxy-benzyl(1R,cis)2,2-dimethyl-3-[Z-2-(cyclopropyloxycarbonyl)-ethenyl]-cyclopropane-carboxylate melting at 62° C.

NMR Spectrum (deuterochloroform): Peaks at 1.27–1.3 ppm (hydrogens of geminal methyls); at 3.25 to 3.4 ppm (3-hydrogen of cyclopropyl); at 1.94–2.08 ppm (1-hydrogen of cyclopropyl); at 6.4 to 6.5 ppm (1-hydrogen of allyl); at 5.8–6.0 ppm (2-hydrogen of allyl);

at 6.4 ppm (hydrogen on carbon attached to —CN); at 7 to 7.7 ppm (aromatic hydrogens); at 0.7–0.77 ppm (hydrogen of cyclopropyloxycarbonyl).

EXAMPLE 23

(S)α-cyano-3-phenoxy-benzyl(1R,cis)2,2-dimethyl-3-[Z-2-allyloxycarbonyl)-ethenyl]-cyclopropane-carboxylate Using the procedure of Example 7, 2.75 g of (S)α-cyano-3-phenoxy-benzyl(1R,cis)2,2-dimethyl-3-[Z-2-carboxyethenyl]-cyclopropane-carboxylate and 0.8 ml of allyl alcohol were reacted and the mixture was evaporated to dryness under reduced pressure. The residue was chromatographed over silica gel and was eluted with an 8-2 n-hexane-ethyl acetate mixture to obtain 1.25 g of (S)α-cyano-3-phenoxy-benzyl(1R,cis)2,2-dimethyl-3-[Z-2-allyloxycarbonyl)-ethenyl]-cyclopropane-carboxylate with a specific rotation of $[\alpha]_D^{20} = +45° \pm 3°$ (c=0.35% in benzene).

NMR Spectrum (deuterochloroform): Peaks at 1.25–1.27 ppm (hydrogens of geminal methyls); at 3.22 to 3.52 ppm (3-hydrogen of cyclopropyl); at 1.93–2.07 ppm (1-hydrogen of cyclopropyl); at 6.4 to 6.75 ppm (1-hydrogen of allyl); at 5.87–6.06 ppm (2-hydrogen of allyl); at 4.6–4.7 ppm (1-hydrogens of allyl ester); at 5.7 to 6.3 ppm (2-hydrogen of allyl ester); at 5.1 to 5.45 ppm (3-hydrogen of allyl ester); at 6.3 ppm (hydrogen on carbon attached to —CN); at 6.9 to 7.6 ppm (aromatic hydrogens).

EXAMPLE 24

(S)α-cyano-3-phenoxy-benzyl(1R,cis)2,2-dimethyl-3-[Z-2-(propargyloxycarbonyl)-ethenyl]-cyclopropane-carboxylate

STEP A:

Tert.-butyl(1R,cis)2,2-dimethyl-3-[Z-2-(propargyloxycarbonyl)-ethenyl]-cyclopropane-carboxylate Using the procedure of Step A of Example 13, 3.6 g of tert.-butyl(1R,cis)2,2-dimethyl-3-[Z-2-carboxyethenyl]cyclopropane-carboxylate and 1 ml of propargyl alcohol were reacted and the mixture was stirred at 20° C. for 16 hours and was filtered. The filtrate was extracted with methylene chloride and the organic phase was washed with 0.1N hydrochloric acid, with water until the wash water was neutral, dried and evaporated to dryness under reduced pressure. The residue was taken up in a 9-1 cyclohexane-ethyl acetate mixture and the mixture was stirred at 20° C. for 90 minutes and was filtered. The filtrate was evaporated to dryness and the residue was chromatographed over silica gel. Elution with a 9-1 cyclohexane-ethyl acetate yielded 2.1 g of tert.-butyl(1R,cis)2,2-dimethyl-3-[Z-2-(propargyloxy-carbonyl)-ethenyl]cyclopropane-carboxylate.

IR Spectrum (chloroform):

Absorption at 3300 and 2225 cm$^{-1}$ (—C≡C—); at 1712 cm$^{-1}$ (ester carbonyl+conj.); at 1629 cm$^{-1}$ (conj. —C=C—).

STEP B:

(1R,cis)2,2-dimethyl-3-[Z-2-(propargyloxycarbonyl)ethenyl]-cyclopropane-carboxylic acid A mixture of 2.0 g of the product of Step A, 0.2 g of p-toluene sulfonic acid and 20 ml of anhydrous toluene was refluxed for 10 minutes and was cooled to 0° C. and stirred for 30 minutes. The mixture was filtered and the filtrate was evaporated to dyrness under reduced pressure to obtain 1.59 g of (1R,cis)2,2-dimethyl-3-[Z-2-(propargyloxycarbonyl)ethenyl]-cyclopropane-carboxylic acid which was used as is for the next step.

STEP C:

(S)α-cyano-3-phenoxy-benzyl(1R,cis)2,2-dimethyl-3-[Z-2-(propargyloxycarbonyl)-ethenyl]-cyclopropane-carboxylate Using the procedure of Step C of Example 13, 1.59 g of the product of Step A and 1.8 g of (S)α-cyano-3-phenoxy-benzyl alcohol were reacted and after 2 hours, the mixture was filtered. The filtrate was evaporated to dryness under reduced pressure and the residue was chromatographed over silica gel. Elution with a 9-1 cyclohexane-ethyl acetate mixture yielded 2.86 g of (S)α-cyano-3-phenoxy-benzyl(1R,cis)2,2-dimethyl-3-[Z-2-(propargyloxycarbonyl)-ethenyl]-cyclopropane-carboxylate with a specific rotation of $[\alpha]_D^{20} = +44° \pm 1.5°$ (c=1% in CHCl$_3$).

NMR Spectrum (deuterochloroform): Peaks at 1.23–1.27 ppm (hydrogens of geminal methyls); at 1.93–2.07 ppm (1-hydrogen of cyclopropyl); at 3.18 to 3.5 ppm (3-hydrogen of cyclopropyl); at 6.46–6.65 ppm and 6.62–6.82 ppm (1-hydrogen of allyl); at 5.87–6.05 ppm (2-hydrogen of allyl); at 4.72–4.73 (1-hydrogens of propargyl); at 2.47(t) ppm (3-hydrogen of propargyl); at 6.3 ppm (hydrogen on carbon attached to —CN); at 6.92–7.6 ppm (aromatic hydrogens).

Also capable of being produced by the process of the invention are (S)α-cyano-3-phenoxy-benzyl(1R,cis)2,2-dimethyl-3-[Z-2-(n-undecyloxycarbonyl)-ethenyl]-cyclopropane-carboxylate, (S)α-cyano-3-phenoxy-benzyl(1R,cis)2,2-dimethyl-3-[Z-2-(1-methylcyclohexyloxycarbonyl)-ethenyl]-cyclopropane-carboxylate, (S)α-cyano-3-phenoxy-benzyl(1R,cis)2,2-dimethyl-3-[Z-2-(n-hexyloxycarbonyl)-ethenyl]-cyclopropane-carboxylate and (S)α-cyano-3-phenoxy-benzyl(1R,cis)2,2-dimethyl-3-[Z-2-(cyclobutylmethyloxycarbonyl)-ethenyl]-cyclopropane-carboxylate.

EXAMPLE 25

Soluble concentrates were prepared containing 0.25 g of either the product of Example 1 or the product of Example 6, 1 g of piperonyl butoxide, 0.25 g of Tween 80, 0.1 g of Topanol A and 98.4 g of water.

Emulsifiable concentrates were prepared by intimately admixing 0.015 g of the product of Example 1 or the product of Example 6, 0.5 g of piperonyl butoxide, 0.1 g of Topanol A, 3.5 g of Tween 80 and 95.885 g of xylene.

Emulsifiable concentrates were prepared by homogenizing a mixture of 1.5 g of the product of Example 1 or the product of Example 6, 20 g of Tween 80, 0.1 g of Topanol A and 78.4 g of Xylene.

Smoke producing compositions were prepared containing 0.25 g of the product of Example 1 or the product of Example 6, 25 g of tabu powder, 40 g of cedar-needle powder, 33.75 g of pine-wood powder, 0.5 g of brilliant green and 0.5 g of p-nitrophenol.

EXAMPLE 26

An antifungal composition in the form of a wettable powder was prepared from 20 g of (1R,cis)2,2-dimethyl-3-[Z-2-(methoxycarbonyl)-ethenyl]-cyclopropane-carboxylic acid, 15 g of Ekapersol S (condensation product of sodium naphthalene sulfonate), 0.5 g of Brecolane NVA (sodium alkyl naphthalene sulfonate), 32.5 g of Zeosil 39 (precipitated synthetic hydrated silica) and 25 g of Vercoryl (S) (colloidal Kaolin).

An antifungal composition in the form of a solution was prepared containing 25 g/l of (1R,cis)2,2-dimethyl-3-[Z-2-(methoxycarbonyl)-ethenyl]-cyclopropane-carboxylic acid, 80 g/l of Emcol H 300 B and 895 g/l of Xylene.

PESTICIDAL STUDIES

A. Insecticidal activity on houseflies

The test was effected on 4 day old female houseflies which received a topical application of 1 μl of an acetone solution of the test compound on the dorsal thorax with an Arnold micro-manipulator. 50 insects were used for each test and the number of dead insects was determined after 24 hours to calculate the $LD_{50}$ dose in nanograms (the dose killing 50% of the insects). The results are reported in Table I.

TABLE I

| Compound of Example | $LD_{50}$ in ng |
|---|---|
| 1 | 7.128 |
| 3 | 3.494 |
| 5 | 2.781 |

The results of Table I show that the tested compounds have a good insecticidal activity against houseflies.

B. Activity against *Spodoptera littoralis* larvae

The test was carried out on larvae of *Spodoptera littoralis* by applying an acetone solution of the test compound with an Arnold micro-manipulator to the dorsal thorax of the larvae. 10 to 15 larvae were used for each tested dose and the larvae were in the fourth stage (about 10 days old at 24° C. and 65% relative humidity). The larvae were then placed in an artifical medium (Poitout medium) and the number of dead were determined after 48 hours to calculate the $LD_{50}$ in ng. The results are reported in Table II.

TABLE II

| Compound of Example | $LD_{50}$ in ng |
|---|---|
| 1 | 3.602 |
| 3 | 3.260 |
| 5 | 7.920 |

The results of Table II show that the tested compounds had good insecticidal activity against the *Spodoptera littoralis* larvae.

C. Activity against *Epilachna Varivestris* Larvae

The test was carried out by topical application of the test compounds as in test B and the larvae of *Epilachna Variestris* were in second last stage. The treated larvae were then placed on bean plants and the number of dead was determined after 72 hours to calculate the $LD_{50}$ in ng. The results are reported in Table III.

TABLE III

| Compound of Example | $LD_{50}$ in ng |
|---|---|
| 1 | 8.290 |
| 3 | 8.850 |
| 5 | 3.705 |
| 6 | 0.446 |

The results of Table III show that the tested compounds, especially the compound of Example 6, had good insecticidal activity against *Epilachna Variavestris* larvae.

D. Knock-down Activity on Houseflies 50 4 day old female houseflies per dose were directly sprayed in a Kearns and March chamber with a solution of the 0.25 g/l of the test compound in 2 ml of a mixture of 5% of acetone and Isopar L (petroleum solvent) in one second. After 15 minutes, the $KT_{50}$ was determined and the results are reported in Table IV.

TABLE IV

| Compound of Example | $KT_{50}$ in mins. |
|---|---|
| 1 | 1.226 |
| 3 | 3.340 |
| 5 | 4.390 |

The results of Table IV show that the tested compounds, and especially the compound of Example 1, have a remarkable knock-down activity.

E. Activity against *Tetranychus Urticae*

2 leaves of bean plants were infested with 25 female *Tetranychus Urticae* per leaf and the plants were placed in a ventilated hood under a constant luminous ceiling. The plants were treated with a Fischer pistol with 4 ml per plant of a 1—1 water acetone mixture of the test compound and the plants were allowed to dry for 12 hours. Infestation was then proceeded with and the number of dead were determined after 80 hours. The $LD_{50}$ was determined by a preliminary test of 3 doses and a second test for 5 doses. The $LD_{50}$ for the product of Example was 0.586 g/hl which was a remarkable acaricidal activity.

F. Activity against *Boophilus Microplus* larvae

A 10% emulsifiable concentrate was prepared by dissolving the test compound of Example 6 in a mixture of dimethylformamide, emulsifiers and Arcopal and the concentrate was diluted with water to obtain solutions of 10,5 and 1 ppm of active compound. The different solutions were sprayed by a spraying tower on to larvae of tropical cattle ticks of the *Boophilus Microplus* type (Mexico sensitive and DDT resistant strains) and the number of dead and live larvae was determined after 24 hours. The results are reported in Table V.

TABLE V

| Dose of compound of Example 6 in ppm | % Mortality Mexico Sensitive | % Mortality DDT Resistant |
|---|---|---|
| 10 | 100 | 100 |
| 5 | 100 | 100 |
| 1 | 100 | 100 |

The results of Table V show that the compound of Example 6 shows remarkable activity against *Boophilus Microplus* larvae.

G. Activity against *Rhipicephalus appendiculatus* and *Amblyomma hebraeum* ticks The test procedure of F was repeated with the compound of Example 6 at doses of 100, 10 and 1 ppm using 10 ticks of *Rhipicephalus appendiculatus* or *Amblyomma hebraeum* per test as above. The results are reported in Table VI.

TABLE VI

| Dose in ppm | % Mortality (Rhip. app.) | % Mortality (Ambl. heb) |
|---|---|---|
| 100 | 100 | 100 |
| 10 | 100 | 100 |
| 1 | 100 | 70 |

The results of Table VI show that the compound of Example 6 possesses excellant tickicide activity against *Rhipicephalus appendiculatus* and *Amblyomma hebraeum*.

H. Inhibition of reproduction of *Boophilus Microplus* ticks

Female *Boophilus Microplus* ticks of the Mexico sensitive strain ready to lay eggs were immersed for 5 minutes in solutions of 100, 50, 25, 12.50 and 6.25 ppm of the compound of Example 6 and then they were placed in a heated enclosure to lay their eggs. The percentage of ticks who did not lay, the amount of eggs laid as a function of one control and the percentage of larvae which hatched after 2 weeks were determined and the percentage of reproduction inhibition was calculated therefrom. 100% indicated total inhibition and 0% was the controls and the results are reported in Table VII.

TABLE VII

| Dose in ppm | % inhibition |
|---|---|
| 100 | 100 |
| 50 | 100 |
| 25 | 100 |
| 12.50 | 100 |
| 6.25 | 100 |

The results of Table VII show that the compound of Example 6 has a remarkable tickicide activity.

I. Antifungal Activity

The antifungal activity of (1R,cis)2,2-dimethyl-3-[Z-2-(methoxycarbonyl)-ethenyl]-cyclopropane-carboxylic acid was determined in an adhesive test using an aqueous 3% carboxymethyl starch solution. The test compound was dissolved in 1 ml of acetone and 5 ml of an innoculum consisting of a mixture of spores of *Fusarium Roseum, Penicillium Roquefonti* and *Aspergilus Niger* were added thereto. The development of fungus after 48 hours and 8 days was compared to an untreated control on a scale of 3 to 0. The results are reported in Table VIII.

TABLE VIII

| % Concentration | Growth of Fungus after 48 hours | 8 days |
|---|---|---|
| 0.05 | 0 | 0 |
| 0.01 | 3 | 3 |
| Control | 3 | 3 |

The results of Table VIII show that the tested compound had good anti-fungal activity.

J. Anti-fungal test on oils

A solution of 3% of synthetic fluid was used to test the anti-fungal activity of (1R,cis)2,2-dimethyl-3-[Z-2-(methoxycarbonyl)-ethenyl]-cyclopropane-carboxylic acid and contamination was effected with 5 ml of an innoculum consisting of a mixture of spores of Geotrichum, Trichosporon and Cephalosporium. The check was carried out quantitatively and the results are reported in Table IX.

TABLE IX

| % Concentration | Anti-fungal growth after 48 hours | 8 days |
|---|---|---|
| 1 | 0 | |
| 0.5 | 0 | |
| Control | 49 × 10³ Geo. + 80 × 10³ Tri. + 11 × 10³ Cep. | 33 × 10³ Geo. + 15 × 10³ Tri. |

The results of Table IX show that the tested compound had good antifungal activity.

K. Bactericidal Activity

The bactericidal activity of (1R,cis)2,2-dimethyl-3-[Z-2-(methoxycarbonyl)-ethenyl]-cyclopropane-carboxylic acid was determined with a solution of 3% of carboxymethyl starch in water. The test compound was placed in 1 ml of water and 5 ml of an innoculum of a mixture of spores of *Aerobacter Aerogenes, Pseudomonas Aeruginosa, Escherichia Coli, Serratia Mancescens* and *Bacillus Subtilis* were added thereto. The mixture was placed in an oven for 48 hours at 37° C. and then for 6 days at 20° C. The bacterial population (coloress ml) was determined 48 hours and 8 days by the serum dihibition method and incorporation into broth containing agar. The results are reported in Table X.

TABLE X

| Population after 48 hours | | | after 8 days | | |
|---|---|---|---|---|---|
| 0.05% | 0.025% | Control | 0.05% | 0.025% | Control |
| 52 × 10² | 10 × 10⁴ | 12 × 10⁷ | 68 × 10⁴ | 16 × 10⁶ | 16 × 10⁷ |

The results of Table X show that the tested compound had a good bactericidal activity.

Various modifications of the products and methods of the invention may be made without departing from the spirit or scope thereof and it is to be understood ahat the invention is intended to be limited only as defined in the appended claims.

We claim:

1. A compound having the formula

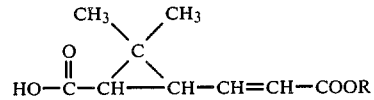

wherein R is selected from the group consisting of alkyl of 1 to 8 carbon atoms, alkenyl and alkynyl of 2 to 8 carbon atoms and optionally unsaturated cycloalkyl and cycloalkylalkyl of 3 to 8 carbon atoms optionally substituted with at least one alkyl and the double bond in the 3-side chain has the Z geometry.

2. An antifungal and biocidal composition comprising a biocidally and antifungicidally effective amount of at least one compound of claim 1 and a carrier.

3. The composition of claim 2 wherein the compound is (1R,cis)2,2-dimethyl-3-[Z-2-(methoxycarbonyl)-ethenyl]cyclopropane-carboxylic acid.

4. A method of controlling fungus comprising contacting fungus with a fungicidally effective amount of at least one compound of the formula

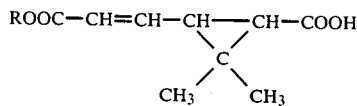

wherein R is selected from the group consisting of alkyl of 1 to 8 carbon atoms, alkenyl and alkynyl of 2 to 8 carbon atoms and optionally unsaturated cycloalkyl and cycloalkylalkyl of 3 to 8 carbon atoms optionally substituted with at least one alkyl and the double bond in the 3-side chain has the Z geometry.

5. The method of claim 4 wherein the compound is (1R,cis)2,2-dimethyl-3-[Z-2-(methoxycarbonyl)-ethenyl]-cyclopropane-carboxylic acid.

6. A method of combatting bacteria comprising contacting bacteria with a bactericidally effective amount of at least one compound of the formula

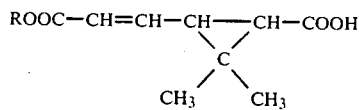

wherein R is selected from the group consisting of alkyl of 1 to 8 carbon atoms, alkenyl and alkynyl of 2 to 8 carbon atoms and optionally unsaturated cycloalkyl and cycloalkylalkyl of 3 to 8 carbon atoms optionally substituted with at least one alkyl and the double bond in the 3-side chain has the Z geometry.

7. The method of claim 6 wherein the compound is (1R,cis)2,2-dimethyl-3-[Z-2-(methoxycarbonyl)-ethenyl]cyclopropane-carboxylic acid.

* * * * *